US010478485B2

(12) United States Patent
Ketter et al.

(10) Patent No.: US 10,478,485 B2
(45) Date of Patent: Nov. 19, 2019

(54) METHODS AND COMPOSITIONS TO PREVENT OR TREAT BACTERIAL INFECTIONS

(71) Applicants: Patrick Ketter, San Antonio, TX (US); Bernard Arulanandam, San Antonio, TX (US); Neal Guentzel, San Antonio, TX (US)

(72) Inventors: Patrick Ketter, San Antonio, TX (US); Bernard Arulanandam, San Antonio, TX (US); Neal Guentzel, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/741,069

(22) PCT Filed: Jul. 1, 2016

(86) PCT No.: PCT/US2016/040738

§ 371 (c)(1),
(2) Date: Dec. 29, 2017

(87) PCT Pub. No.: WO2017/004545

PCT Pub. Date: Jan. 5, 2017

(65) Prior Publication Data

US 2018/0193442 A1 Jul. 12, 2018

Related U.S. Application Data

(60) Provisional application No. 62/187,722, filed on Jul. 1, 2015.

(51) Int. Cl.

| | |
|---|---|
| ***A61K 39/104*** | (2006.01) |
| ***A61K 39/05*** | (2006.01) |
| ***A61K 31/04*** | (2006.01) |
| ***C12N 1/36*** | (2006.01) |
| ***C12N 1/20*** | (2006.01) |
| ***A61P 31/04*** | (2006.01) |
| ***A61K 39/00*** | (2006.01) |
| ***C12N 9/02*** | (2006.01) |

(52) U.S. Cl.

CPC ............ *A61K 39/104* (2013.01); *A61K 39/05* (2013.01); *A61P 31/04* (2018.01); *C12N 1/20* (2013.01); *C12N 1/36* (2013.01); *C12N 9/0036* (2013.01); *C12N 9/0051* (2013.01); *C12Y 108/01009* (2013.01); *A61K 2039/522* (2013.01); *A61K 2039/54* (2013.01); *A61K 2039/575* (2013.01)

(58) Field of Classification Search

CPC .......... A61K 2300/00; A61K 2039/522; A61K 2039/575; A61K 31/16; A61K 31/47; A61K 38/12; A61K 39/05; A61K 39/104; A61K 2039/54; A61K 45/06; A61K 2039/70; A61K 31/7088; A61K 39/0233; C12N 1/36; C12N 1/20; C12N 9/0036; C12N 9/0051; A61P 31/04; C12Y 108/01009; G01N 2500/10; G01N 2333/195; G01N 33/56911; Y02A 50/401; Y02A 50/402; Y02A 50/469; Y02A 50/471; Y02A 50/573; Y02A 50/475; Y02A 50/478; Y02A 50/48; Y02A 50/481; Y02A 50/403; C07K 14/22; C07K 14/29; C07K 2319/00; C07K 2319/03; C07K 2319/21; C07K 2319/23; C07K 2319/40; C07K 2319/70

See application file for complete search history.

(56) References Cited

U.S. PATENT DOCUMENTS

| | | | | |
|---|---|---|---|---|
| 2004/0161809 | A1 | 8/2004 | Aharonowitz et al. | |
| 2010/0028334 | A1 * | 2/2010 | Cottarel ................ | A61K 31/16 514/1.1 |
| 2012/0301474 | A1 | 11/2012 | Spellberg et al. | |

FOREIGN PATENT DOCUMENTS

| | | |
|---|---|---|
| WO | WO 2015/009699 | 1/2015 |
| WO | WO 2015/052350 | 4/2015 |

OTHER PUBLICATIONS

International Written Opinion and Search Report issued in Application No. PCT/US2016/040738, dated Sep. 9, 2016.
International Preliminary Report on Patentability issued in Application No. PCT/US2016/040738, dated Jan. 2, 2018.
Taglietti et al., "Novel Topical Drug Delivery Systems and Their Potential Use in Acne Vulgaris," *Skin Ther. Lett.*, 2008; 13:6-8 Accessed Mar. 26, 2018 [http://www.skintherapyletter.com/conditions/acne/novel-topical-drug-delivery-systems/].
Villers et al., "Nosocomial *Acinetobacter baumannii* Infections: Microbiological and Clinical Epidemiology," *Annals of Internal Medicine*, 1998; 129(3): 182-189.

* cited by examiner

*Primary Examiner* — Sarvamangala Devi
(74) *Attorney, Agent, or Firm* — Norton Rose Fulbright US LLP

(57) ABSTRACT

Certain embodiments are directed to methods and compositions for preventing treating bacterial infections. In certain embodiments the compositions comprise thioredoxin deficient bacteria.

8 Claims, 29 Drawing Sheets

| | | Percent Survival (%) | Individual Time to Death (Days) |
|---|---|---|---|
| C57BL/6 | (n=7) | 71.4 | 2, 10, 12, 13 (2), >30 (2) |
| C57BL/6: IgA$^{-/-}$ | (n=7) | 42.9 | 8 (2), 10, >30 (4) |

| Bacteria | MIC (µg/mL) | MBC (µg/mL) |
|---|---|---|
| CI77 | 31.25 | 31.25 |
| CI78 | 62.5 | 62.5 |
| CI79 | 31.25 | 31.25 |
| CI80 | 31.25 | 31.25 |
| CI86 | 31.25 | 31.25 |

FIG. 6

| Strain | MIC Doxycycline | MIC PX-12 | MBC Doxycycline | MBC PX-12 |
|---|---|---|---|---|
| *A. baumannii* CI 77 | 32 | 16 | 64 | 16 |
| *A. baumannii* CI 78 | 1 | 32 | 8 | 32 |
| *A. baumannii* CI 79 | 16 | 16 | 32 | 16 |
| *A. baumannii* CI 80 | 8 | 16 | 32 | 16 |
| *A. baumannii* CI 86 | 16 | 16 | 16 | 32 |
| *A. baumannii* ATCC 19606 | <0.5 | 8 | 4 | 16 |
| *E. coli* ATCC 25922 | 1 | 16 | 32 | 16 |

FIG. 10

METHODS AND COMPOSITIONS TO PREVENT OR TREAT BACTERIAL INFECTIONS

STATEMENT REGARDING FEDERALLY FUNDED RESEARCH

This invention was made with government support under contract W911NF-11-1-0136 awarded by the Army Research Office of the US Department of Defense. The government has certain rights in the invention.

This application is a national phase application under 35 U.S.C. § 371 of International Application No. PCT/US2016/040738, filed Jul. 1, 2016, which claims priority to U.S. Provisional Application 62/187,722 filed Jul. 1, 2015. Both applications are incorporated herewith in their entirety.

BACKGROUND

*Acinetobacter baumannii* infections account for 34% of wound infections seen in soldiers injured while fighting in the Middle East. Over the last half century, the prevalence of wound infections caused by this and other Gram-negative bacterial infections have been on the rise due to the use of antibiotics on the battlefield. Today, these organisms have become the predominant pathogens recovered from war wounds sustained by soldiers due to their natural resistance to many common antimicrobials. This has been exacerbated in the case of *Acinetobacter baumannii* through the development of multi-drug resistant (MDR) strains. Although uncommon as a gastrointestinal pathogen, colonization of the gastrointestinal tract by *Acinetobacter baumannii* has been linked to the development of MDR strains. As a result, *Acinetobacter baumannii* is of major concern, not only on the battlefield, but also in hospitals and clinics, leading many to adopt screening protocols to prevent its spread.

Because of the ability of *Acinetobacter baumannii* to colonize the gastrointestinal tract, and its prevalence in wound infections seen in soldiers overseas, the inventors questioned whether it may explain some of the symptoms reported from veterans from the Persian Gulf War suffering from Gulf War Illness (GWI). GWI is a multifactorial disease presenting with a variety of symptoms. Gastrointestinal complications have been reported in some cases of GWI. Soldiers returning from the Persian Gulf may have suffered severe trauma and developed infections caused by organisms such as *Acinetobacter baumannii*, which can be very difficult to treat due to intrinsic antibiotic resistance.

There remains a need for additional compositions and therapies for treating bacterial infections.

SUMMARY

Methods and compositions are provided that can be used to prevent or treat bacterial infections. In certain embodiments the compositions comprise attenuated *Acinetobacter*. In certain aspects the *Acinetobacter* is *Acinetobacter baumannii* and/or *Acinetobacter calcoaceticus*. In a further aspect the attenuated *Acinetobacter* is deficient in thioredoxin-A (TrxA). In still a further aspect the *Acinetobacter* comprises a full or partial deletion in the TrxA coding region or gene, resulting in a non-functional TrxA gene. In other embodiments the TrxA gene can be mutated to abolish or reduce the function of the TrxA protein, with the reduction of function being to a level that results in the attenuation of the bacteria. Certain aspects are directed to methods of administering anti-bacterial compositions to patients before exposure or shortly after exposure to bacterial agents. The term "shortly after" refers to administering treatment within 1, 12, 24, 36, 48, 60, or 72 hours, or 1, 2, 3, 4, 5, 6, or 7 days after suffering trauma (e.g., open wound) or presentation of gastrointestinal symptoms. Such treatment can depress the viability or virulence of bacterial agents and prevent, mitigate, or hinder infection, or the development of disease caused by these bacterial agents. In certain aspects the bacterial agent is an *Acinetobacter*. In a further aspect the bacterial agent is a live attenuated *Acinetobacter baumannii*. As used herein, the term "live attenuated vaccine" or "live attenuated bacteria" is known in the art and refers to a vaccine containing live micro-organisms that have attenuated or decreased virulent properties or which contains closely-related but less virulent organisms to evoke a broad immune response.

Certain embodiments are directed to methods of treating or preventing *Acinetobacter baumannii* colonization or infection comprising administering a clinically effective dose of an attenuated bacteria to a subject in need thereof. Certain embodiments are directed to methods of treating or preventing *Acinetobacter baumannii* colonization or infection comprising administering a clinically effective dose of an attenuated *Acinetobacter baumannii* to a subject in need thereof. In certain aspects, the attenuated *Acinetobacter baumannii* is deficient in thioredoxin-A. In certain aspects, the attenuated *Acinetobacter baumannii* is administered before the administration of an antimicrobial agent. In certain aspects, the attenuated *Acinetobacter baumannii* is administered orally. In certain aspects, the attenuated *Acinetobacter baumannii* is administered as a live attenuated *Acinetobacter baumannii*. In some embodiments a composition (e.g., vaccine) is formulated for effective administration through inclusion of additional agents such as excipients, adjuvants, preservatives, stabilizing agents, salts, buffering agents, immunogenic agents, and the like.

In some embodiments, the method for treating or preventing bacterial infection in a subject involves administering a bacterial composition described herein.

In some embodiments, the composition used for treating or preventing bacterial infection is formulated for effective administration through inclusion of additional agents (e.g., adjuvants, preservatives, stabilizing agents, salts, buffering agents, immunogenic agents). In certain aspects the method for treating or preventing bacterial infection is not limited to any particular dose or treatment regime. The composition may be administered at least once; twice; three times; four times; 5-10 times; 10-20 times; 20-100 times; 100 times or more. In further aspects the method is not limited by the duration of time between repetitive administrations of the composition or by the duration of time between administration of the composition and challenge or exposure to a pathogenic agent. The duration of time may be 0 days; 1 day; 2 days; 3 days; 4 days; 5 days; 5-7 days; 1-2 weeks; 2-4 weeks; 4-8 weeks; 8-10 weeks; 10-31 weeks; 31-52 weeks; 1-5 years; 5-10 years; 10-20 years; 20-50 years; 50-100 years or more. In some embodiments, the subject is tested for the presence of an infection prior to administration of the composition. In some embodiments, the subject is not tested for the presence of an infection prior to the administration of the composition. In some embodiments, the subjected is tested for infection following administration of the composition. Such testing may be conducted less than one day, 1-2 days, 2-4 days, 4-6 days, 6-8 days, 8-10 days, 10-15 days, 15-20 days, 20-30 days, 30 or more days prior to administration of the composition.

Certain embodiments are directed to a *Acinetobacter baumannii* that is deficient in thioredoxin-A (trx-A). Certain embodiments are directed to a vaccine. In certain aspects, the vaccine contains attenuated *Acinetobacter baumannii*, wherein the attenuated *Acinetobacter baumannii* is *Acinetobacter baumannii* deficient in thioredoxin-A (Δtrx-A). In certain aspects, the vaccine contains live attenuated *Acinetobacter baumannii*. In certain aspects, the vaccine is formulated for oral administration. In certain aspects, the vaccine is formulated for vaccination against *Acinetobacter baumannii*.

In some embodiments compositions and methods of administering these compositions to patients are intended to be used before exposure or after exposure to bacterial agents such as *Acinetobacter baumannii*. In certain embodiments the patient has an *Acinetobacter* infection. In certain aspects the patient has an *Acinetobacter baumannii* infection. In still other aspects the patient is diagnosed with or has a high probability of being diagnosed with *Acinetobacter baumannii* infection. In some instances the patient is suspected of being exposed to *Acinetobacter baumannii* in a hospital or other medical facility. In certain aspects the patient is at risk of infection, i.e., the patient is physically located, was wounded in, or was present in a location or facility that harbors or has harbored *Acinetobacter baumannii*. In a further aspect the patient is on mechanical ventilation, has sustained traumatic injuries, and/or is burned. In certain embodiments the patient is identified as having a previous or current gastrointestinal colonization by *Acinetobacter*. In certain aspects the patient has been wounded. In a further aspect a patient or subject is a veterinary patient or subject, e.g., livestock such as goat, cattle, sheep; or domesticated animal such as dogs and cats.

In still other aspects the patient is diagnosed with or has a high probability of being diagnosed with *Acinetobacter baumannii* wound colonization or infection.

In still other aspects the patient is diagnosed with or has a high probability of being diagnosed with *Acinetobacter baumannii* related pneumonia.

In still other aspects the patient is diagnosed with or has a high probability of being diagnosed with *Acinetobacter baumannii* that is resistant to antibiotics or other conventional anti-microbial drugs.

As used herein, "colonized" or "colonization" refers to the subclinical presence of bacteria in a patient, whereas "infected," "infection," or "diseased" refers to disease or an overt clinical manifestation of infection, i.e., change in structure or physiology, leading to damage in any body site. Subclinical infection is the asymptomatic presence of a bacterium in an individual that may causes illness, at least in some individuals. Since subclinical infections occur without overt signs, their existence can be identified by microbiological culture or nucleic acid detection techniques such as polymerase chain reaction. Clinical disease is an infection that presents various symptoms that can be used to diagnose infection.

The term "treating" or "treatment" of an infection or disease refers to ameliorating the infection (i.e., arresting the growth of the bacteria or reducing the manifestation, extent or severity of at least one of the clinical symptoms thereof). "Preventing infection" means that substantially no symptoms of infection are detected after exposure of the subject to bacteria that can cause infections.

The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof. In addition, if desired, the compositions can contain minor amounts of auxiliary substances such as wetting or emulsifying agents, and/or pH buffering agents, which enhance the effectiveness of the compositions.

In some embodiments, methods further comprise testing the patient for *Acinetobacter baumannii* infection or diagnosing a patient with *Acinetobacter baumannii* infection. Additional methods may also involve treating a patient with other *Acinetobacter baumannii* treatments such as standard antibiotic treatments.

Certain embodiments are directed to a method of evaluating or classifying a subject relative to severity of infection or risk of sepsis. The method comprising contacting a sample with a pentraxin-related protein 3 (PTX3) binding or affinity reagent and detecting the amount of complex between the binding agent and PTX3 present in a sample. The method can also comprised identifying the subject as at risk for disease or sepsis if the level of PTX3 is elevated significantly above the levels of a non-infected subject or a reference. Pentraxin 3 (ptx3) is a member of the pentraxin superfamily, which is characterized by a cyclic multimeric structure.

In certain aspects a biological sample is from a subject suspected of having a disease or condition associated with *Acinetobacter* infection. In a further aspect the subject is an immunosuppressed, immunocompromised, or immunodeficient subject.

In certain aspects the affinity reagent (biomarker specific reagent) is an affinity reagent (e.g., an antibody, aptamer, oligonucleotide probe, etc.) that specifically forms a complex with PTX3. The reagent/biomarker complex can then be identified, detected, and/or measured. In certain aspects the reagent/biomarker complex is directly or indirectly coupled to a detectable label.

The methods can further comprise comparing the presence or level of PTX3 to a reference, wherein an altered presence or level relative to the reference provides a diagnostic for *Acinetobacter* infection. The reference can be from a biological sample from a subject not having or at risk of infection, or a calculated threshold or reference. The reference can be from a series of biological samples measured at one or more different time points.

As used herein the term "detect" (including variations thereof, e.g., "detecting") refers to determining the presence of or level of a biomarker, e.g., a nucleic acid, polypeptide or functional fragment thereof, in a biological sample or series of a biological samples. The sample or samples are obtained from a subject in order to detect a condition or disease or detect likelihood of a condition or disease. The term "functional fragment(s)" in respect to a biomarker can mean a portion of a molecule or complex used as a biomarker that is identifiable and may be less than the whole but sufficient to detect whether the biomarker is present and/or level of the biomarker present. For example, a functional fragment can be a polypeptide fragment (e.g., peptide) or nucleic acid molecule sequence that can be identified.

A "biological sample" means a sample of biological tissue or fluid. Examples of biological samples are sections of tissues, blood, blood fractions, plasma, serum, urine or samples from other peripheral sources. Furthermore, also pools or mixture of the above mentioned samples may be employed. A biological sample may be provided by removing a sample from a subject. In certain embodiments, a blood sample is taken from the subject. In certain aspects the biological sample preferably is a blood or a serum sample.

"Polynucleotide," also referred to as "nucleic acid molecule" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, double-stranded, or a mixture of single- and double-stranded regions. "Polynucleotide" also embraces relatively short nucleic acid chains, often referred to as oligonucleotides.

"Polypeptide" refers to any peptide or protein comprising amino acids joined by peptide bonds or modified peptide bonds. "Polypeptide" refers to short chains, including peptides, oligopeptides or oligomers, and to longer chains, including proteins. Polypeptides may contain amino acids other than the 20 gene-encoded amino acids. "Polypeptides" include amino acid sequences modified either by natural processes, such as post-translational processing, or by chemical modification or other synthetic techniques well known in the art. Modifications can occur anywhere in a polypeptide, including the peptide backbone, the amino acid side-chains and the amino terminus or the carboxy terminus. It will be appreciated that the same type of modification may be present in the same or varying degrees at several sites in a given polypeptide.

Reagents and/or biomarkers can be labeled or otherwise conjugated to various chemical or biomolecule moieties, for example, for therapeutic or diagnostic or detection or treatment applications. The moieties can be detectable labels, for example, fluorescent labels, radiolabels, biotin, and the like, which are known in the art.

Polynucleotides and polypeptides can be labeled with fluorophores. There are a wide variety of fluorophore labels that can usefully be attached to components of the present invention. For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), TEXAS RED, Cy3, Cy5, fluorescence resonance energy tandem fluorophores such as PerCPCy5.5, PE-Cy5, PE-Cy5.5, PE-Cy7, PE-TEXAS RED, and APC-Cy7. Other fluorophores include, inter alia, Alexa Fluor® 350, Alexa Fluor® 488, Alexa 25 Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, TEXAS RED (available from Molecular Probes, Inc., Eugene, Oreg., USA), and Cy2, Cy3, Cy3.5, Cy5, Cy5.5, Cy7, all of which are also useful for fluorescently labeling the antibodies of the present invention. For secondary detection using labeled avidin, streptavidin, captavidin or neutravidin, the antibodies of the present invention can usefully be labeled with biotin. When the antibodies of the present invention are used, e.g., for western blotting applications, they can usefully be labeled with radioisotopes, such as $^{33}P$, $^{32}P$, $^{35}S$, $^{3}H$, and $^{125}I$.

Moieties of the invention, such as polypeptides, peptides, antigens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation."

"Prognosis" refers to a prediction of how a patient will progress, and whether there is a chance of recovery. "Prognosis" generally refers to a forecast or prediction of the probable course or outcome of the infection. Prognosis includes the forecast or prediction of any one or more of the following: duration of survival of a patient susceptible to or diagnosed with infection, duration of recurrence-free survival, duration of progression-free survival of a patient susceptible to or diagnosed with infection, response rate in a group of patients susceptible to or diagnosed with infection, or duration of response in a patient or a group of patients susceptible to or diagnosed with infection. Prognosis also includes prediction of favorable responses to treatments. A good or bad prognosis may, for example, be assessed in terms of patient survival or likelihood of disease recurrence. In one embodiment, a good or bad prognosis may be assessed in terms of overall survival, disease-free survival or progression-free survival.

The phrase "specifically binds" or "specifically immunoreactive" to a target refers to a binding reaction that is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of a reagent or an antibody to a target or biomarker under such conditions requires the reagent or antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane, Antibodies: A Laboratory Manual, Cold Spring Harbor Press, 1988, for a description of immunoassay formats and conditions that can be used to determine specific immunoreactivity.

Other embodiments of the invention are discussed throughout this application. Any embodiment discussed with respect to one aspect applies to other aspects as well and vice versa. Each embodiment described herein is understood to be embodiments that are applicable to all aspects of the invention. It is contemplated that any embodiment discussed herein can be implemented with respect to any device, method, or composition, and vice versa. Furthermore, systems, compositions, and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 6 shows the antimicrobial effect of PX-12 on *Acinetobacter baumannii.*

FIG. 10 shows a repeat minimum inhibitory concentration (MIC) experiment performed to CLSI standards: Mueller Hinton broth cation adjusted ($Ca^{++}$25 mg/L, $Mg^{++}$12.5 mg/L), bacterial concentration reduced to ~$5\times10^5$ CFU/mL, compound concentrations tested range from 64 to 0.5 μg/mL, low MIC combined with low MBC indicates PX-12 compound has bactericidal activity.

DESCRIPTION

Figures 1A, 1B, 1C, 1D:
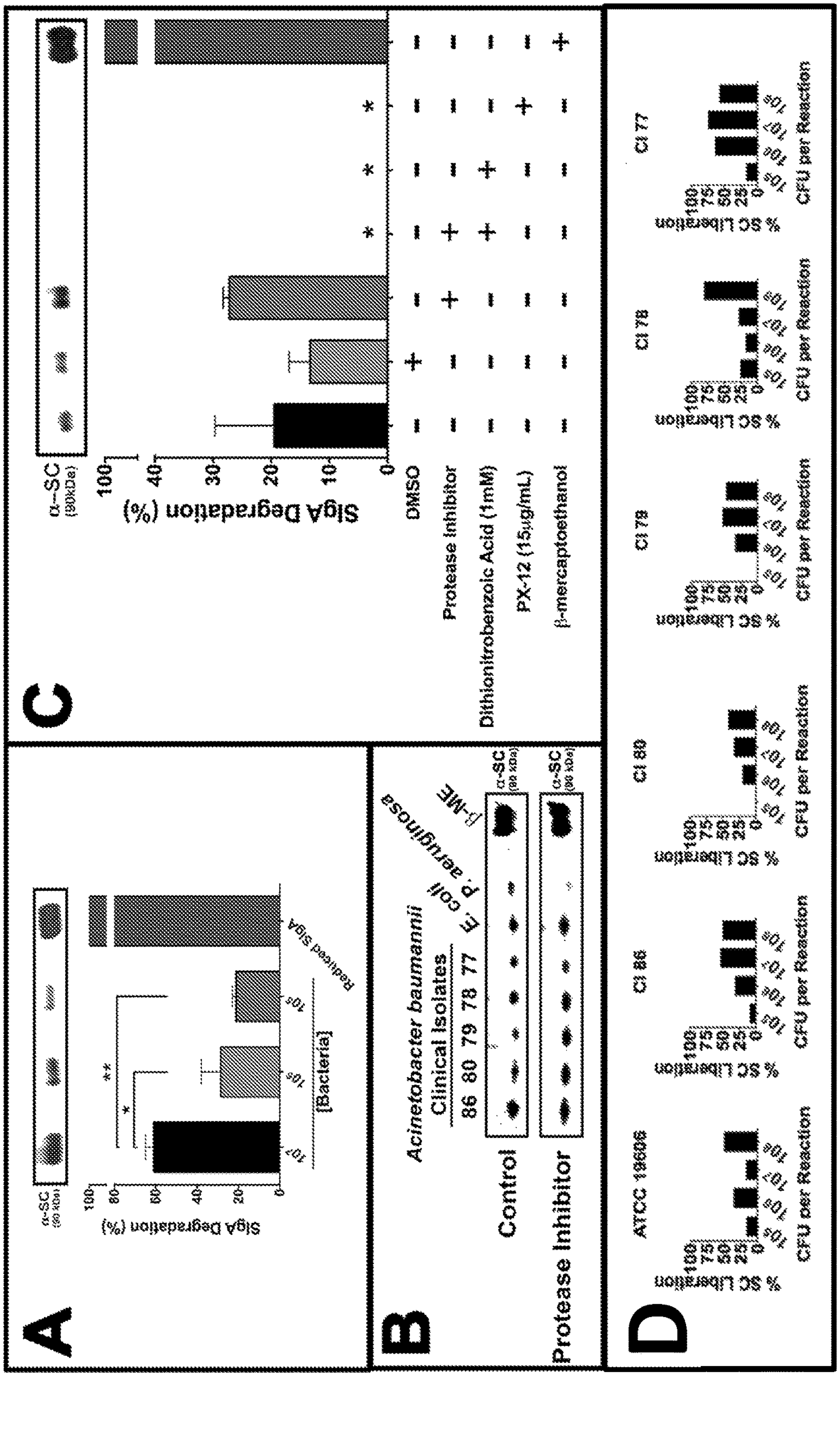
FIG. 1 shows *Acinetobacter baumannii* dissociates Secretory Component (SC) from SIgA through a reductive process.

Immunoglobulin A (IgA) is an antibody that plays a critical role in mucosal immunity. IgA can exist in a dimeric form, which is called secretory IgA (SIgA). In its secretory form, IgA is the main immunoglobulin found in mucosal secretions, including tears, saliva, colostrum and secretions from the genitourinary tract, gastrointestinal tract, prostate and respiratory epithelium. The secretory component of SIgA protects the immunoglobulin from being degraded by proteolytic enzymes, thus SIgA can survive in the harsh gastrointestinal tract environment and provide protection against microbes that multiply in body secretions. Case studies and recent literature suggest a potential link between gastrointestinal (GI) colonization and acquired antimicrobial resistance potentially following *Acinetobacter baumannii* breakdown of SIgA. Breakdown of SIgA has been shown to have an immunosuppressive effect, due to the liberation of secretory component (SC) from SIgA and subsequent inhibition of neutrophil recruitment (Mantis et al. Annals of Internal Medicine, 1998. 129(3):182-189). The breakdown of SIgA also aids bacteria in colonization of the intestinal epithelium. The inventors have conducted studies to investigate how *Acinetobacter baumannii* breaks down SIgA and what affect this has on the virulence of the organism in vivo. The data show that SIgA breakdown by *Acinetobacter baumannii* is a reductive process, rather than a proteolytic, and is significantly reduced after addition of the thioredoxin colorimetric substrate DTNB, suggesting it is acting as a competitive inhibitor.

Prevention of *Acinetobacter baumannii* infections is desirable. Inactivated whole cell vaccine as well as OmpA (Omp38) subunit vaccines have shown therapeutic potential. However, neither are approved for use in humans. Herein, the inventors have created a new attenuated *Acinetobacter baumannii* mutant from a multi-drug resistant clinical isolate deficient in thioredoxin-A (TrxA). This organism exhibits markedly reduced virulence in an i.p. sepsis model and has the potential for use as a live vaccine against *Acinetobacter baumannii* infection.

I. *Acinetobacter*

*Acinetobacter* is a genus of Gram-negative bacteria belonging to the *Gammaproteobacteria. Acinetobacter* spp. are non-motile and oxidase-negative, and occur in pairs under magnification. They are important soil organisms, where they contribute to the mineralization of, for example, aromatic compounds. *Acinetobacter* spp. are a source of infection in debilitated patients in the hospital, in particular the species *Acinetobacter baumannii*. Species of the genus *Acinetobacter* are aerobic non-fermentative Gram-negative bacilli. Most strains of *Acinetobacter*, except some of the *A. lwoffii* strain, grow well on MacConkey agar (without salt). Although officially classified as nonlactose-fermenting, they are often partially lactose-fermenting when grown on MacConkey agar. They are oxidase-negative, nonmotile, and usually nitrate negative. Bacteria of the genus *Acinetobacter* are known to form intracellular inclusions of polyhydroxyalkanoates under certain environmental conditions.

FIG. 1 shows *Acinetobacter baumannii* dissociates Secretory Component (SC) from SIgA through a reductive process. *Acinetobacter baumannii* was incubated with 50 μg/mL SIgA to examine breakdown of the immunoglobulin. Breakdown of SIgA by *A. baumannii* was observed by liberation of secretory component from dimeric IgA. Goat anti-human secretory component (free and bound) antibody was used to monitor this occurrence though Western blot. A mixture of *A. baumannii* strain Ci79 was prepared in three concentrations $-10^7$, $10^6$, and $10^5$ CFU/mL—to determine whether SIgA breakdown was dose dependent with respect to bacterial concentration FIG. 1A. Previous literature examining SIgA degradation by Gram-negative pathogens suggested this process was proteolytic in nature so previous experiments were repeated with a single inoculum ($\sim 10^7$ CFU/mL) of each *A. baumannii* clinical isolate in our bacterial library along with *E. coli* (strong reductase) and *P. aeruginosa* (known IgA protease) in the presence or absence of protease inhibitor. Although a reduction of SIgA degradation by *P. aeruginosa* was seen following incubation with protease inhibitor, no difference was observed with any of the other strains tested suggesting *A. baumannii* utilized a process that was not proteolytic in nature to break down SIgA FIG. 1B. Next, two competitive inhibitors of reductase enzymes targeting the thioredoxin fold (-C-X-X-C-) motif typically found in thiol-reductase enzymes (thioredoxin, glutathione, thioredoxin reductase, etc) were identified. The first, dithionitrobenzoic acid (Ellman's reagent) is often used as a colorimetric substrate to monitor thioredoxin activity as it produces a bright yellow color upon cleavage of the disulfide bond within the molecule. The second is PX-12. Both of these inhibitors completely ablated SIgA reduction and SC liberation 2 hours after incubation at concentrations of 1 mM and 15 μg/mL, respectively (FIG. 1C). Although not shown here, inhibition was still evident at 24 hours with Ellman's reagent, PX-12 inhibition seemed to be overcome by the bacteria after about 12 hours. This may suggest that either the bacteria are producing more reductase enzyme eventually overwhelming the concentrations of PX-12 in the mixture, or the observed PX-12 inhibition is not irreversible with respect to the bacterial reductase. (Error bars represent ±SEM in all graphs; statistical differences determined by ANOVA with Dunnett correction; * significance $p<0.01$; ** $p<0.001$).

Figure 2:
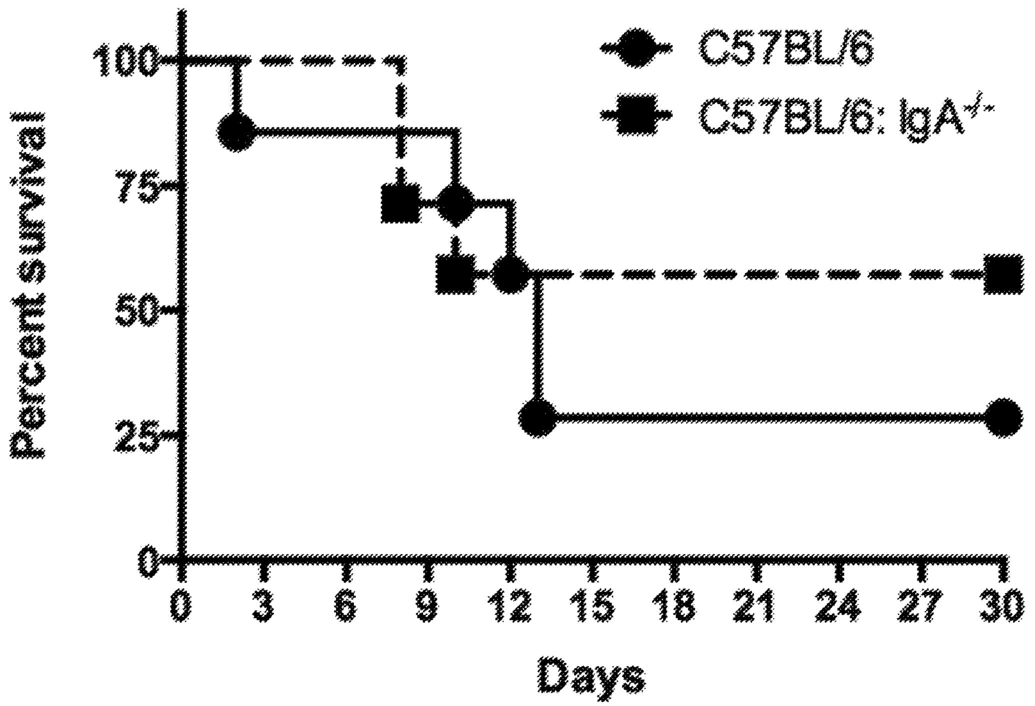
FIG. 2 shows IgA enhances virulence of *Acinetobacter baumannii* during GI challenge.

FIG. 2 shows IgA enhances virulence of *Acinetobacter baumannii* during GI challenge. Wild type (WT) and IgA deficient ($IgA^{-/-}$) C57BL/6 mice were challenged with $5\times10^7$ CFU by oral gavage and monitored for morbidity and mortality over the course of a month. 71% of WT mice challenged succumbed to infection compared to only 43% of $IgA^{-/-}$ mice indicating IgA is necessary for virulence of *Acinetobacter baumannii* during GI challenge (data representative of three independent experiments).

Figures 3A, 3B, 3C:
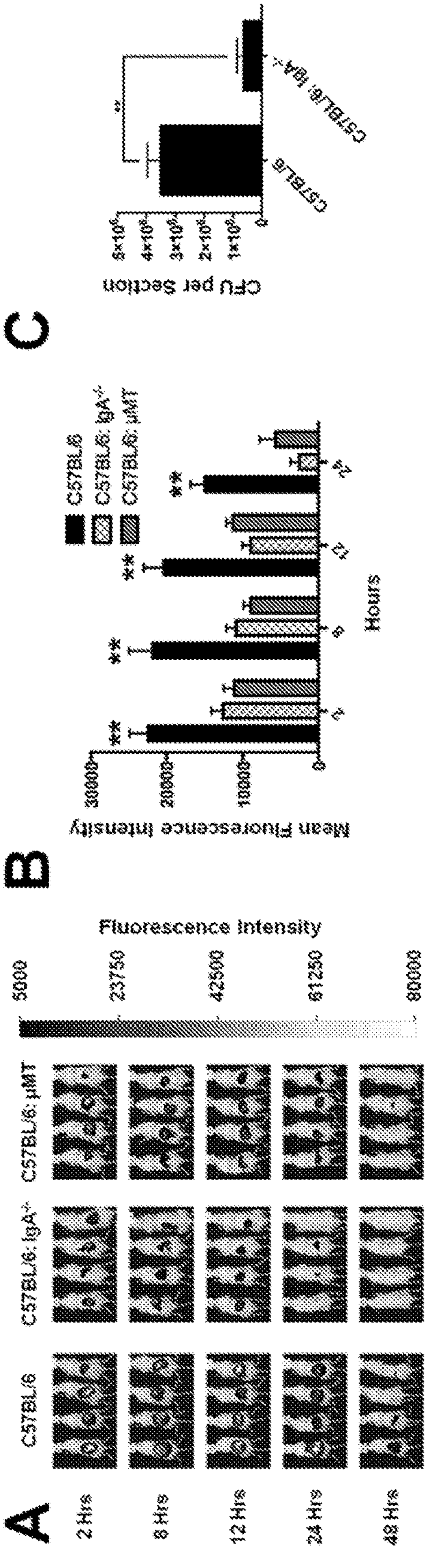
FIG. 3 shows IgA enhances *Acinetobacter baumannii* adherence and colonization in the GI tract.

FIG. 3 shows IgA enhances *Acinetobacter baumannii* adherence and colonization in the GI Tract. *Acinetobacter baumannii* was stained with the cationic dye PSVue®-794, a near-infrared fluorescent dye, and used to track progression of *Acinetobacter baumannii* through the GI tract following oral gavage. Wild type (WT), IgA deficient ($IgA^{-/-}$), and B-cell deficient (μMT) mice were challenged with $5\times10^7$ CFU of the stained bacteria and monitored over the course of two days by full body in vivo live imaging showing prolonged fluorescence in WT mice at all observation points (A). Region of interest (ROI) analysis confirmed these visual differences with significant differences ($p<0.001$) in mean fluorescence intensities associated with WT mice compared to $IgA^{-/-}$ and μMT mice at all observation points (B). Intestinal sections obtained from infant mice also show significantly ($p<0.001$) reduced bacterial adherence in sections from $IgA^{-/-}$ mice compared to WT (C).

Figure 4:
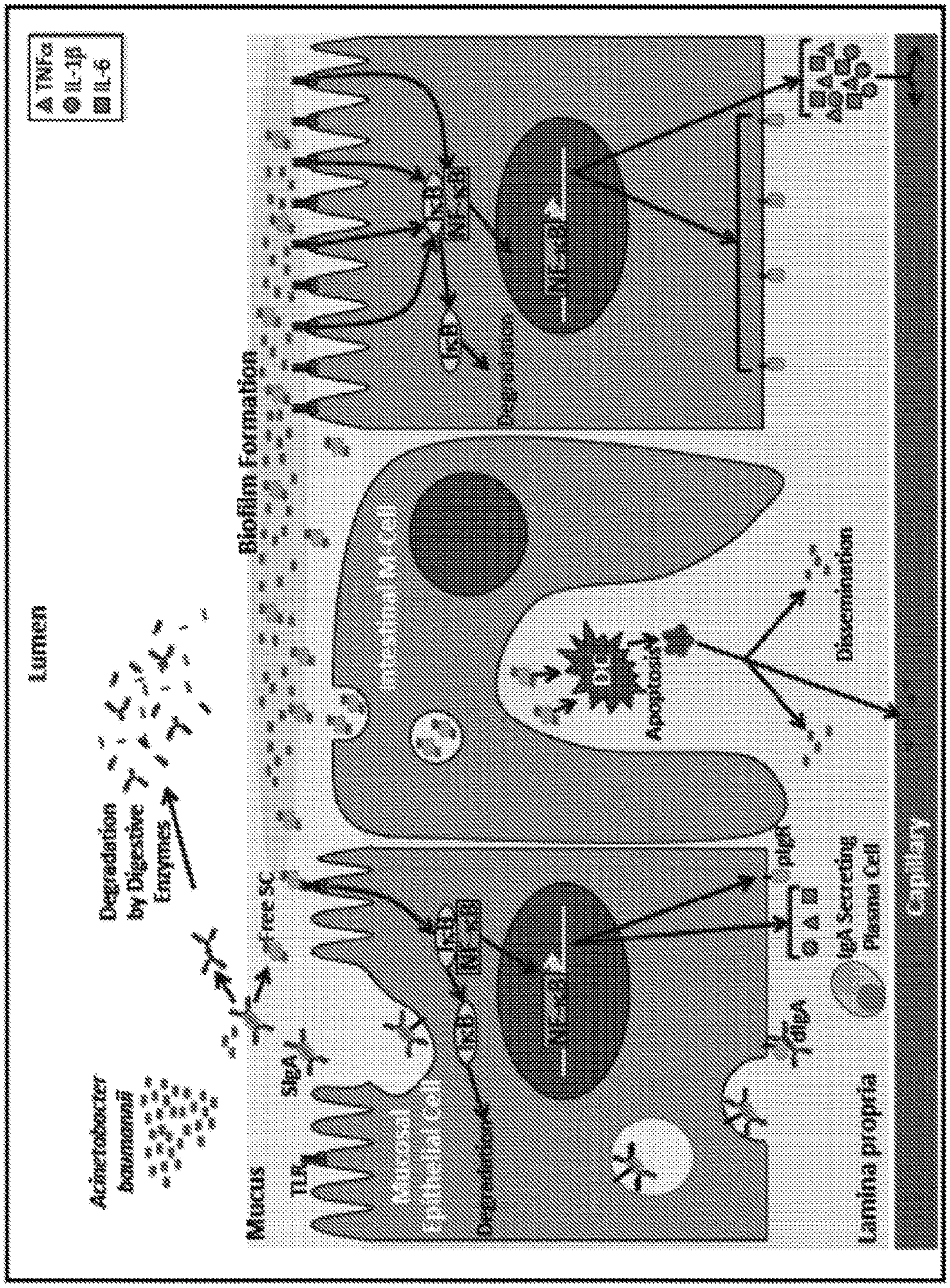
FIG. 4 is a working model of *Acinetobacter baumannii* gastrointestinal infection.

FIG. 4 is a working model of *Acinetobacter baumannii* gastrointestinal infection. Dimeric IgA is produced by IgA secreting plasma cells at the lamina propria of the intestinal epithelium. The polymeric immunoglobulin receptor (pIgR) has high affinity for the J-chain of polymeric immunoglobulins and binds covalently to dimeric IgA. Binding facilitates translocation of the immunoglobulin to the intestinal lumen where pIgR is cleaved and released forming SIgA. During *Acinetobacter baumannii* infection, the bacteria reduce the bonds between the dimeric IgA and SC (the remnant of pIgR still bound to IgA) to form free SC. The unprotected IgA then becomes susceptible to degradation by digestive enzymes while free SC binds to *Acinetobacter baumannii* in a non-specific manner to form immune complexes with the bacteria. These complexes allow the non-motile bacterium to anchor itself within the mucous lining. In so doing, the bacteria can colonize and form biofilms within the gastrointestinal tract. Biofilm formation at the luminal surface of the enterocyte may result in increased TLR activation to stimulate NF-kB activation resulting in increased pro-inflammatory cytokine release and pIgR expression at the basal surface of the cell to allow for increased SIgA. Additionally, the immune complexes formed may be transcytosed by intestinal M-cells for presentation to dendritic cells (DC). If the bacteria are present in high enough numbers, bacterial outer membrane proteins may cause apoptosis in the DCs allowing the bacteria to disseminate into the body.

Figure 5:
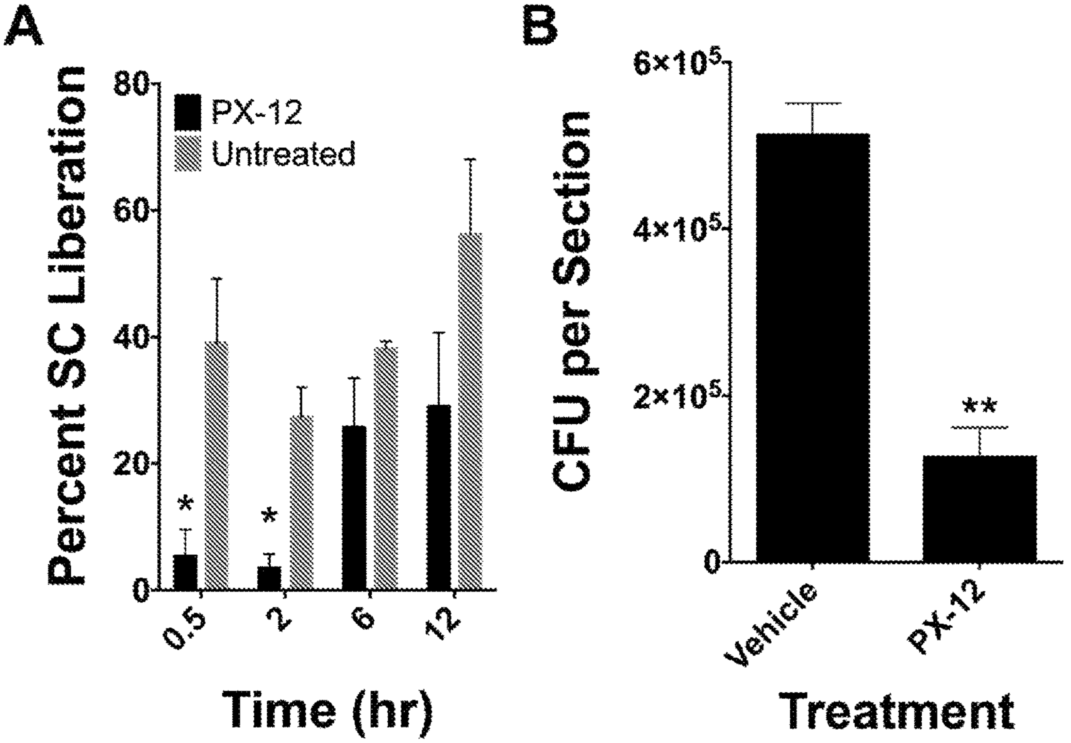
FIG. 5 shows SIgA reduction and intestinal adhesion by *Acinetobacter baumannii* inhibited by thioredoxin inhibitor PX-12.

FIG. 5 shows SIgA breakdown and intestinal adhesion by *Acinetobacter baumannii* is inhibited by thioredoxin Inhibitor PX-12. SIgA breakdown by *Acinetobacter baumannii* is significantly reduced up to 2 hours following treatment with 18 μg/mL PX-12 (A). This same dose significantly inhibits bacterial adherence to intestinal sections obtained from WT C57BL/6 mice (B).

FIG. 6 shows the antimicrobial effect of PX-12 on *Acinetobacter baumannii*. Initial experiments with PX-12 examining the effect of PX-12 on SIgA reduction by *A. buamannii* revealed unexpected results with respect to bacterial growth. PX-12 concentrations used in these experiments approximated the concentration reported "well tolerated" by mice (~500 μg/mouse; 500 μg/mL for this experiment). This dose resulted in a visible decrease in bacterial pellet size when supernatant was collected for analysis. After performing a minimum inhibitor concentration (MIC) determination, the inventors discovered that the MIC for PX-12 with respect to the multi-drug resistant (MDR) *Acinetobacter baumanniii* clinical isolates, with one exception, was 31.25 μg/mL. Furthermore, this concentration was also bactericidal leading us to believe it may potentially be useful as a new antimicrobial compound for treating MDR *Acinetobacter baumannii*. (Bacterial concentrations used in presented studies ~100× higher than recommended by CLSI standards)

Figure 7:
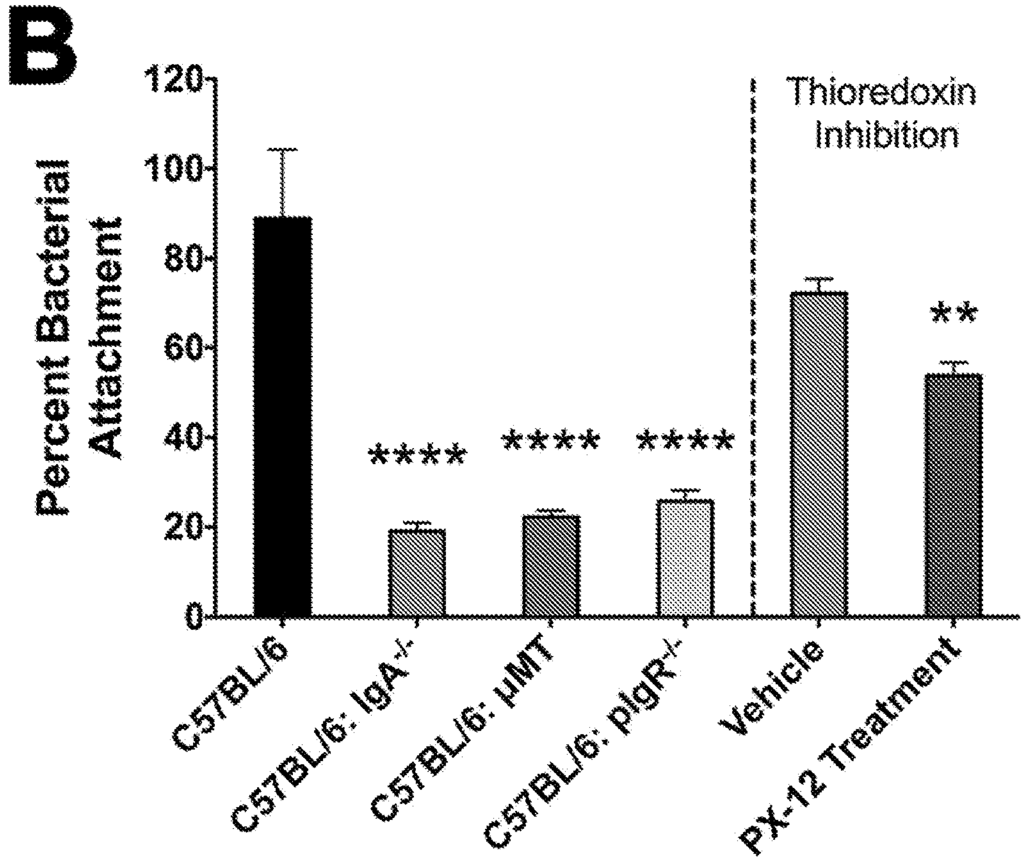
FIG. 7 shows treatment with the mammalian thioredoxin-1 inhibitor PX-12 significantly reduced bacterial attachment by ~40%.

FIG. 7 shows sections of small intestine (mostly duodenal/ileal) from infant WT, $IgA^{-/-}$, $pIgR^{-/-}$, and μMT mice. Intestinal sections were cut down one side to expose the inner lumen of the intestine and individually placed in suspensions of *A. baumannii* strain Ci79 ($10^7$ CFU/mL). The sections were incubated in this mixture for 30 minutes, washed twice in 250 volumes of sterile PBS and soaked in 500 volumes of PBS (volume of section ~50-100 μL) for five minutes. The remaining bound bacteria were enumerated through homogenization of each section into single cell suspensions in 10 mL sterile PBS followed by dilution plating. Using the intestinal sections collected from WT mice as the 100% control, nearly 80% reductions in bacterial adherence were observed in IgA deficient intestinal sections obtained from $IgA^{-/-}$, $pIgR^{-/-}$, and μMT mice compared to WT. Additionally, treatment with the mammalian thioredoxin-1 inhibitor PX-12 also significantly reduced bacterial attachment by ~40%.

Figure 8:
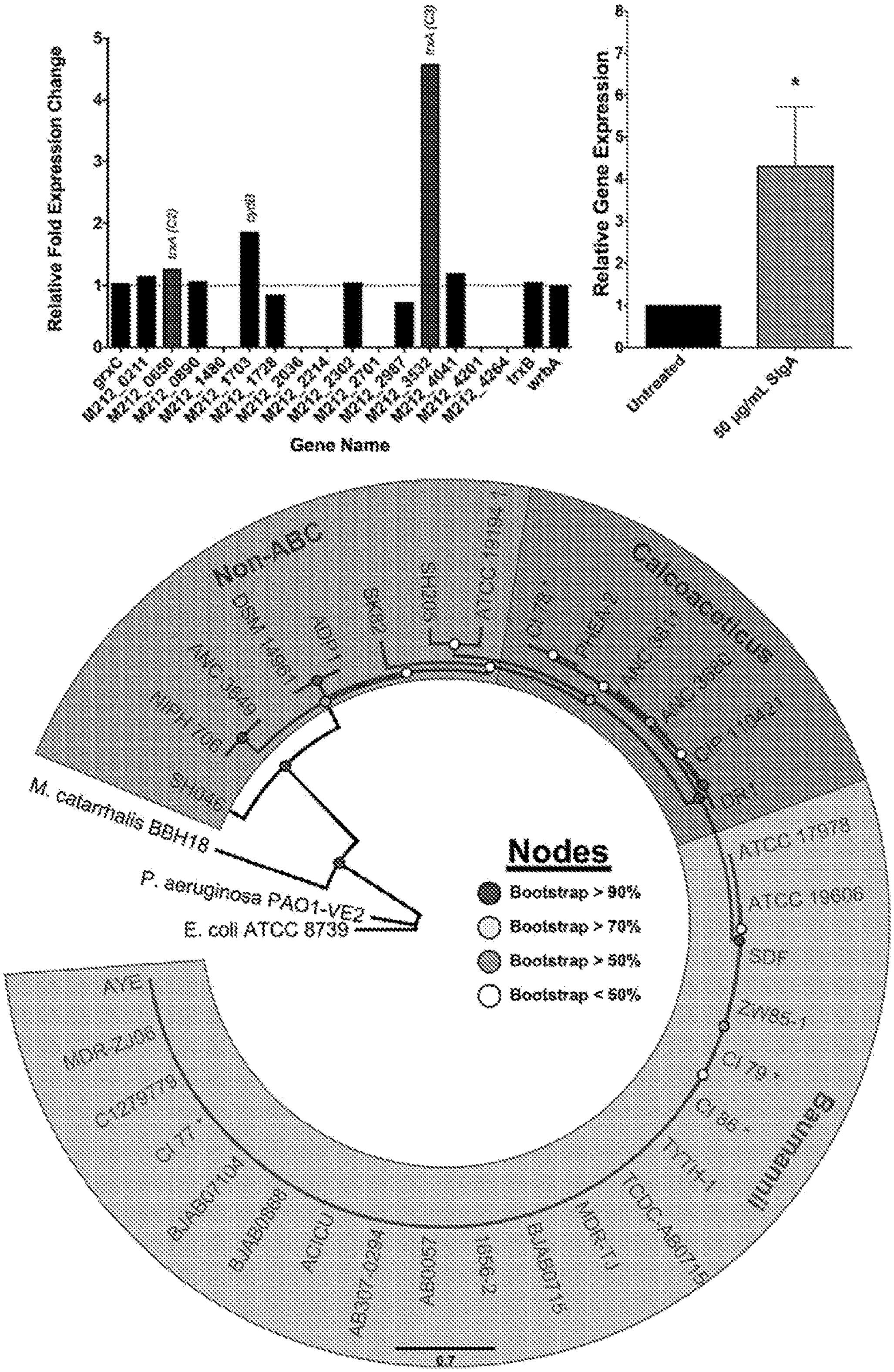
FIG. 8 shows thioredoxin as a mediator of SIgA breakdown

FIG. 8 shows thioredoxin as a mediator of SIgA breakdown. Although inhibition of SIgA reduction was observed with compounds such as dithionitrobenzoic acid and PX-12, both known substrates of thiol-reducing enzymes, there are many *A. baumannii* enzymes classified as reductases. In order to narrow this list of potential mediators of SIgA reduction, RNA sequencing on *A. baumannii* strain Ci79 was performed. The transcriptome expression profile for *A. baumannii* treated for 1 hour with SIgA against untreated *A. baumannii* was assessed using Ion Torrent Personal Genomics Machine (PGM). Eighteen genes involved in reduction-oxidization reactions, based on gene ontology (GO) classifications, were identified and examined for fold change difference in gene expression following SIgA exposure. Of these 18 genes, only one exhibited a fold change greater than 2 following SIgA exposure. This gene, M212_3532, was annotated as thioredoxin-A (trxA), the bacterial homologue to mammalian thioredoxin-1. Although, not as greatly modulated, M212_0650, also annotated as trxA, exhibited increased gene expression (>1). Based on these data, trxA gene expression was examined by quantitative reverse transcription polymerase chain reaction (qRT-PCR) over time. Significantly increased gene expression of trxA (~4.5 fold) 2 hours after exposure to SIgA by the $2^{-\Delta\Delta Ct}$ method was observed (FIG. 8B). Subsequently gene sequences corresponding to trxA in 34 *Acinetobacter* spp. isolates were extracted and assessed for phylogenetic relatedness by PhymL following ClustalW alignment utilizing Geneious analysis software. The resulting phylogenetic tree with corresponding bootstrap values indicated a very high level of genetic conservation between *Acinetobacter* spp. with respect to the thioredoxin-A gene sequence (FIG. 8C). In fact, within the *Baumannii* clade there was nearly 100% sequence homology between strains. Other clades include *Calcoaceticus*, and non-*A. baumannii-calcoaceticus* (non-ABC). (Error bars represent ±SEM (C); statistical difference determined by Welch t-test; * significance $p<0.01$)

Figure 9:
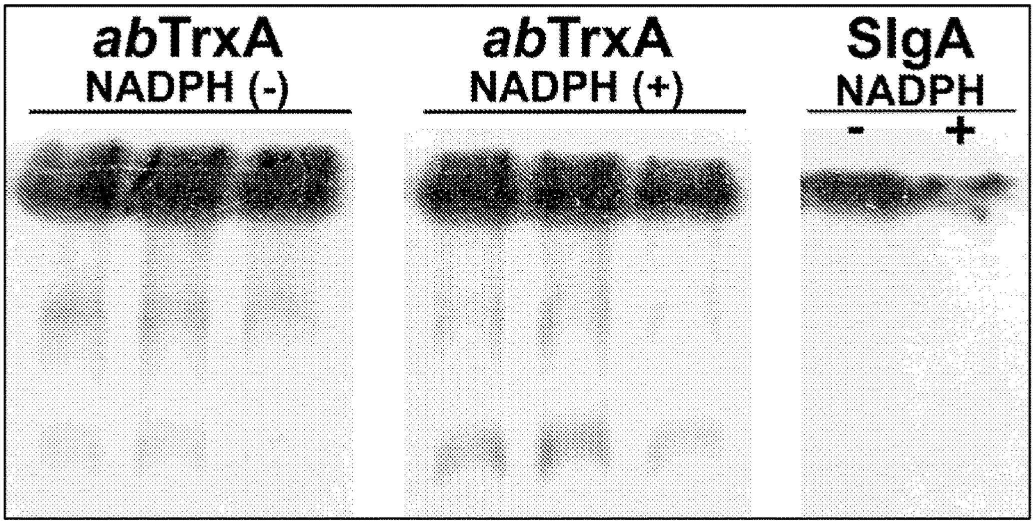
FIG. 9 shows reduction of SIgA by recombinant *A. baumannii* thioredoxin A (abTrxA).

FIG. 9 shows reduction of SIgA by recombinant *A. baumannii* thioredoxin-A (abTrxA). Recombinant abTrxA derived from *A. baumannii* clinical isolate Ci79 was expressed in Rosetta *E. coli* cells and purified using an amylose resin column. Following elution of the protein with maltose, *E. coli* derived thioredoxin reductase (ecTrxB) was found to have eluted with the purified protein. As a result, although reduction of SIgA was observed in the absence of NADPH (left), reduction of SIgA was enhanced with addition of 400 μM NADPH (center). NADPH had no effect on SIgA in the absence of recombinant protein (right). This pattern of SIgA reduction was identical to that observed with bacteria alone.

II. Attenuated *Acinetobacter baumannii* and Vaccines

The inventors have created a new attenuated *Acinetobacter baumannii* mutant from a multi-drug resistant clinical isolate deficient in thioredoxin-A (TrxA). The inventors have discovered that the attenuated *Acinetobacter baumannii* possess decreased virulence and can be used in a vaccine to prevent *Acinetobacter baumannii* infection. The vaccine can be administered as a vaccine and/or in conjunction with the administration of an antimicrobial agent, such as the ones described herein or other known in the art. The vaccine can be administered to a subject orally, parenterally, by inhalation spray, nebulizer, topically, rectally, nasally, buccally, etc. The inventors have discovered that live attenuated *Acinetobacter baumannii* can be used to vaccinate a subject.

Figure 11:
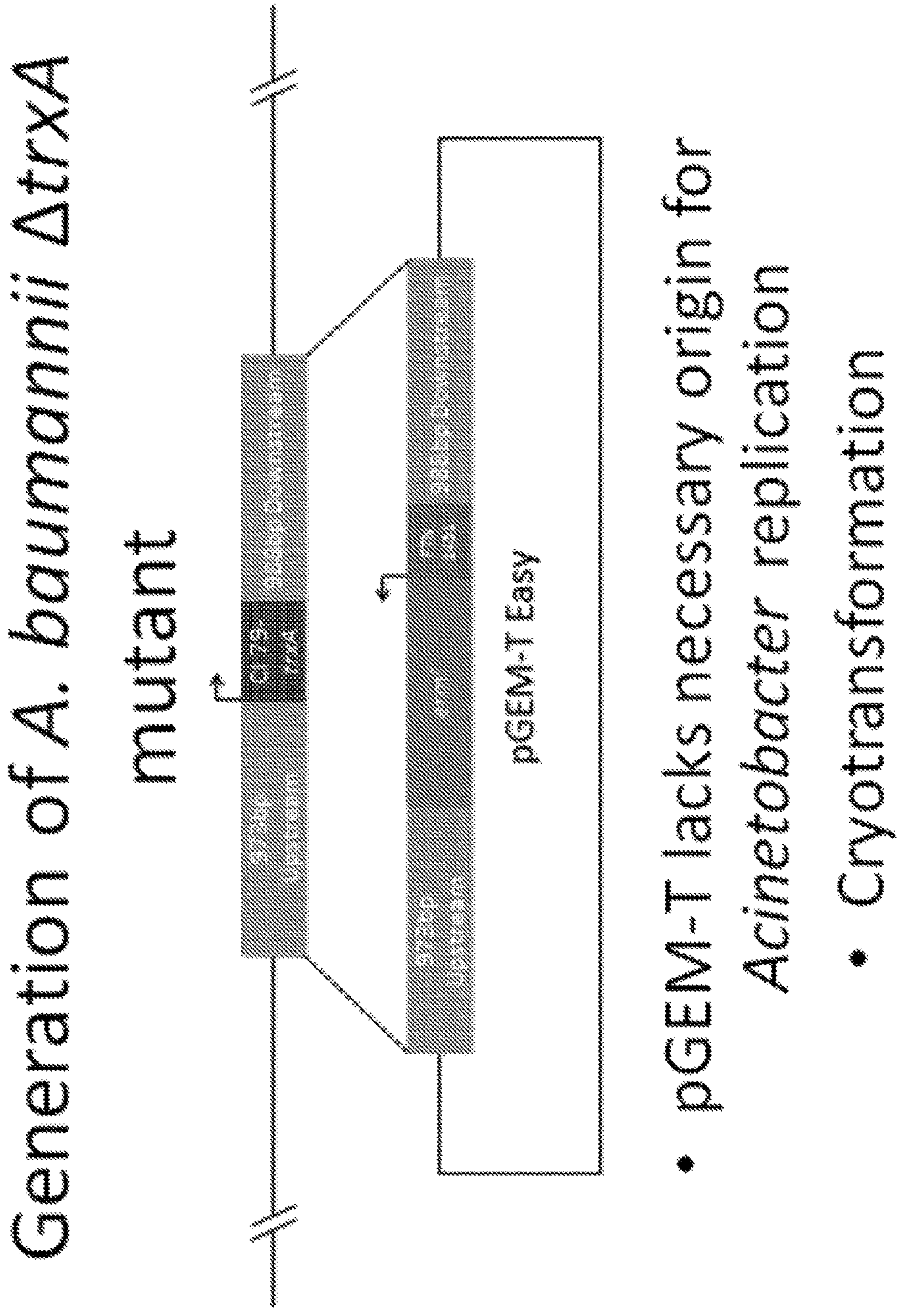
FIG. 11 shows a method used for producing attenuated *Acinetobacter baumannii* deficient in TrxA (ΔtrxA).

FIG. 11 shows a non-limiting example of a method for producing attenuated *Acinetobacter baumannii* deficient in TrxA (ΔtrxA). pGEM-T Easy lacks the necessary origin for *Acinetobacter* replication. In this example, cryotransformation was used and ΔtrxA bacteria were screened by erthyromycin resistance conveyed by the $erm^r$ gene used to replace TrxA.

Figure 12:
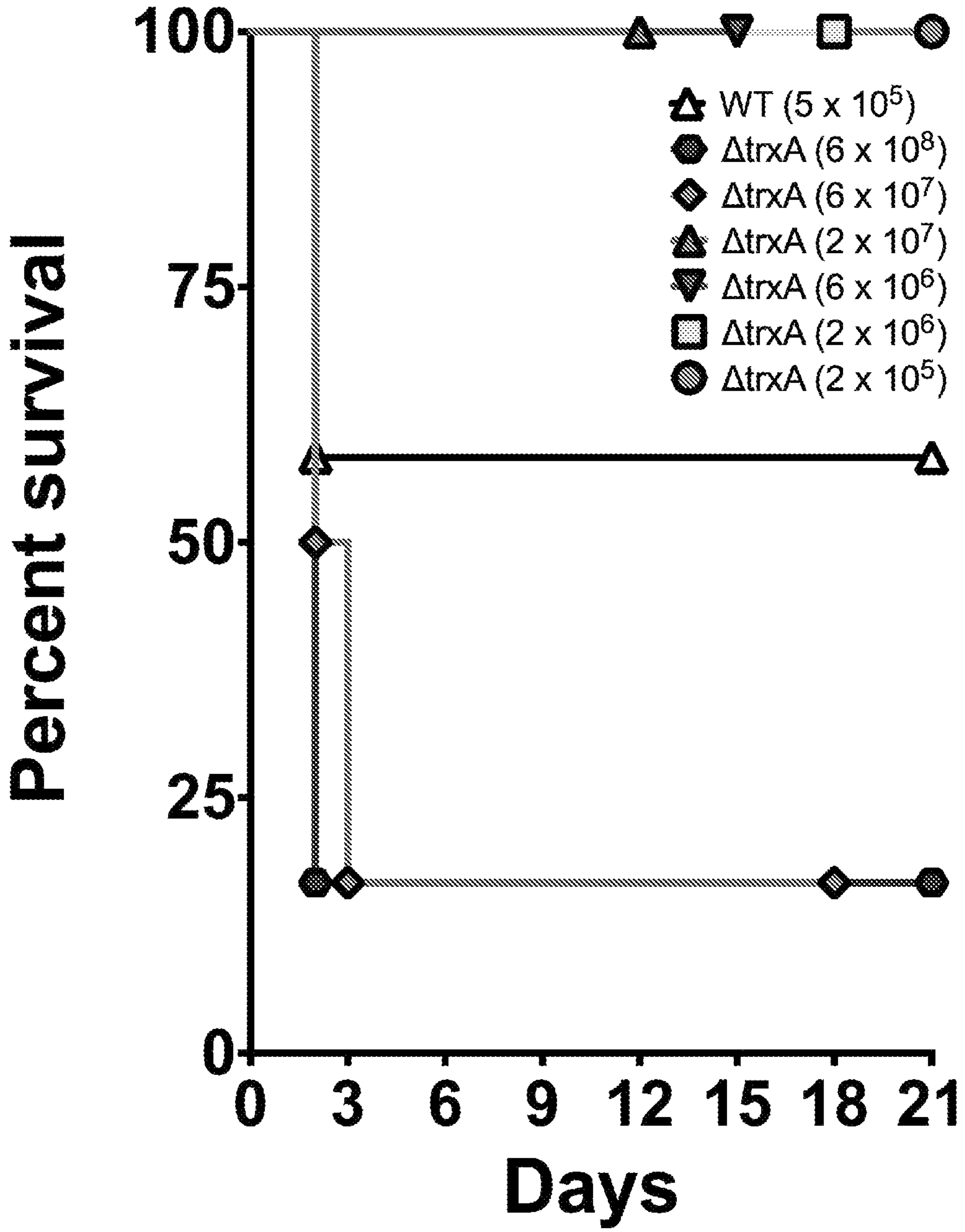
FIG. 12 shows that the virulence of attenuated *Acinetobacter baumannii* is decreased in comparison to wild type (WT) strains in mice.

FIG. 12 shows that the virulence of attenuated *Acinetobacter baumannii* is decreased in comparison to wild type (WT) strains in mice in a sepsis challenge orally dosed with either WT or ΔtrxA. ΔtrxA doses of $2\times10^7$ and less showed no virulence in this assay.

Figure 13:
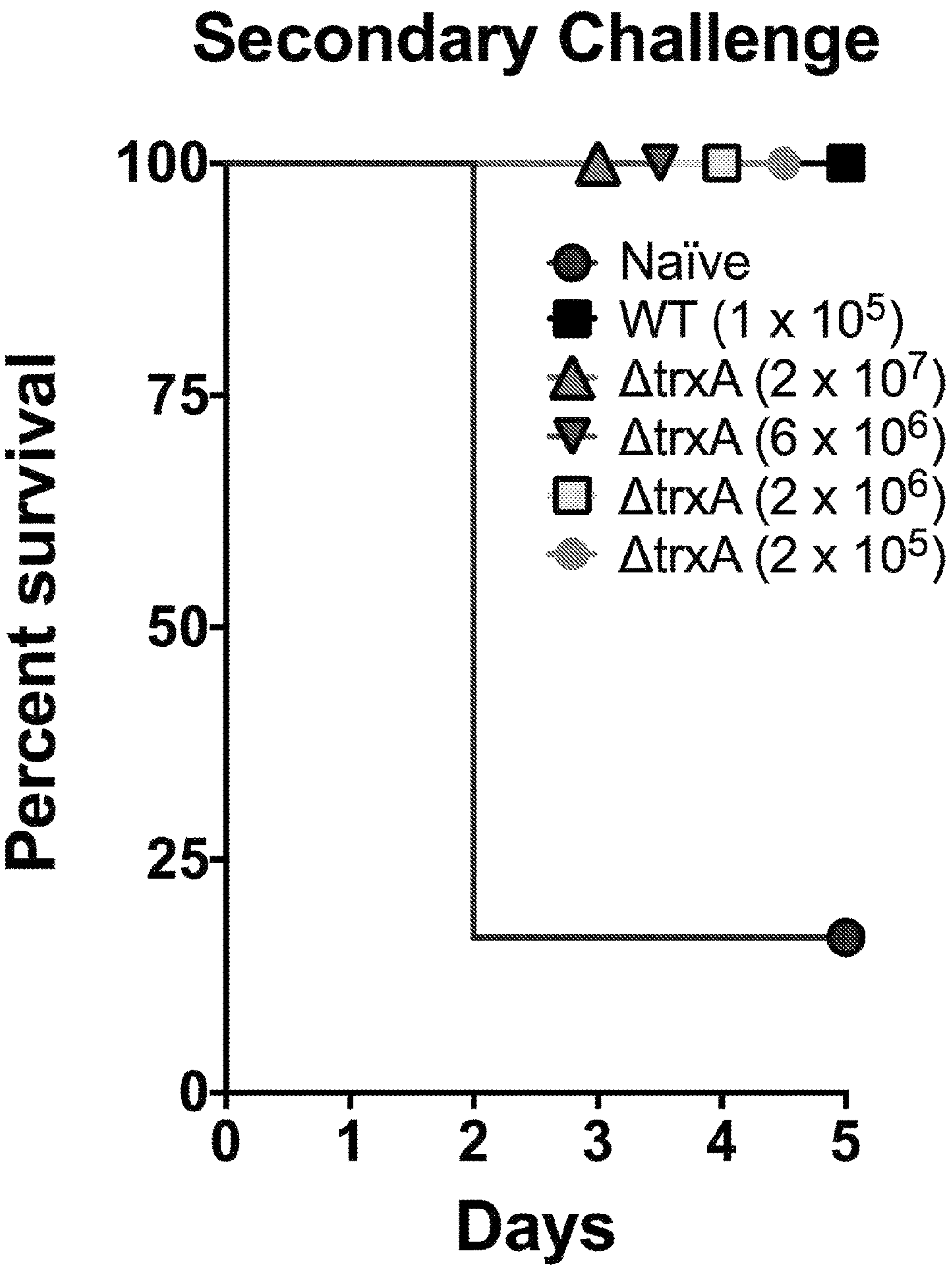
FIG. 13 shows that surviving mice from the sepsis challenge showed increased survival rates in a secondary sepsis challenge.

FIG. 13 shows that surviving mice from the sepsis challenge described in FIG. 11 showed increased survival rates in a secondary sepsis challenge using an otherwise lethal dose of *Acinetobacter baumannii* than mice not previously exposed to any form of *Acinetobacter baumannii* (naïve).

Figure 14:
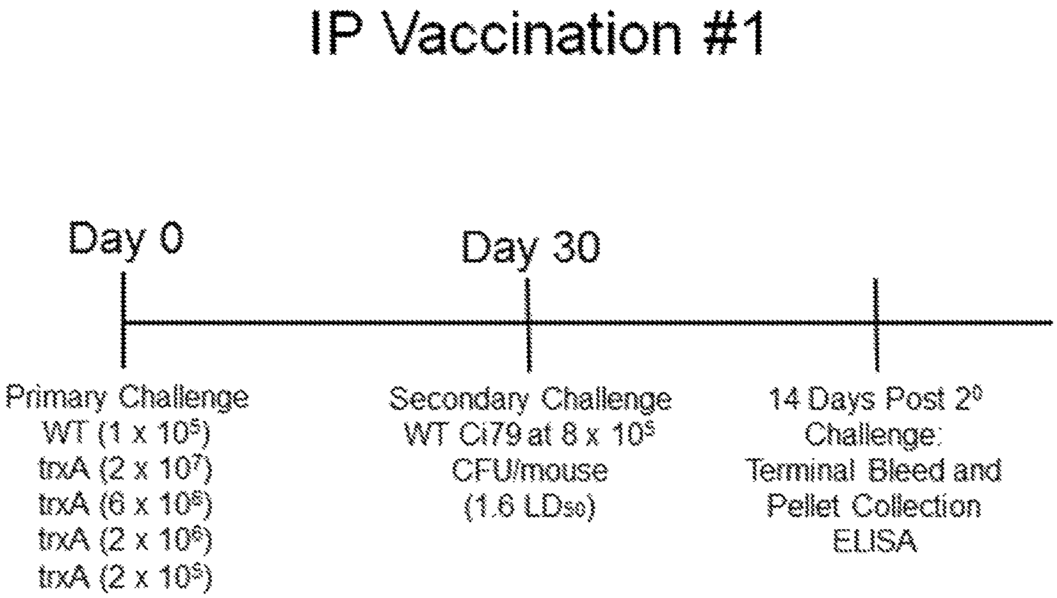
FIG. 14 shows an i.p. vaccination sepsis model used to test the effectiveness of live attenuated *Acinetobacter baumannii* as a vaccine.

FIG. 14 shows an i.p. vaccination sepsis model used to test the effectiveness of live attenuated *Acinetobacter baumannii* as a vaccine against an otherwise lethal dose of *Acinetobacter baumannii* (WT Ci79 at $8\times10^5$ CFU/mouse (1.6 $LD_{50}$)).

Figure 15:
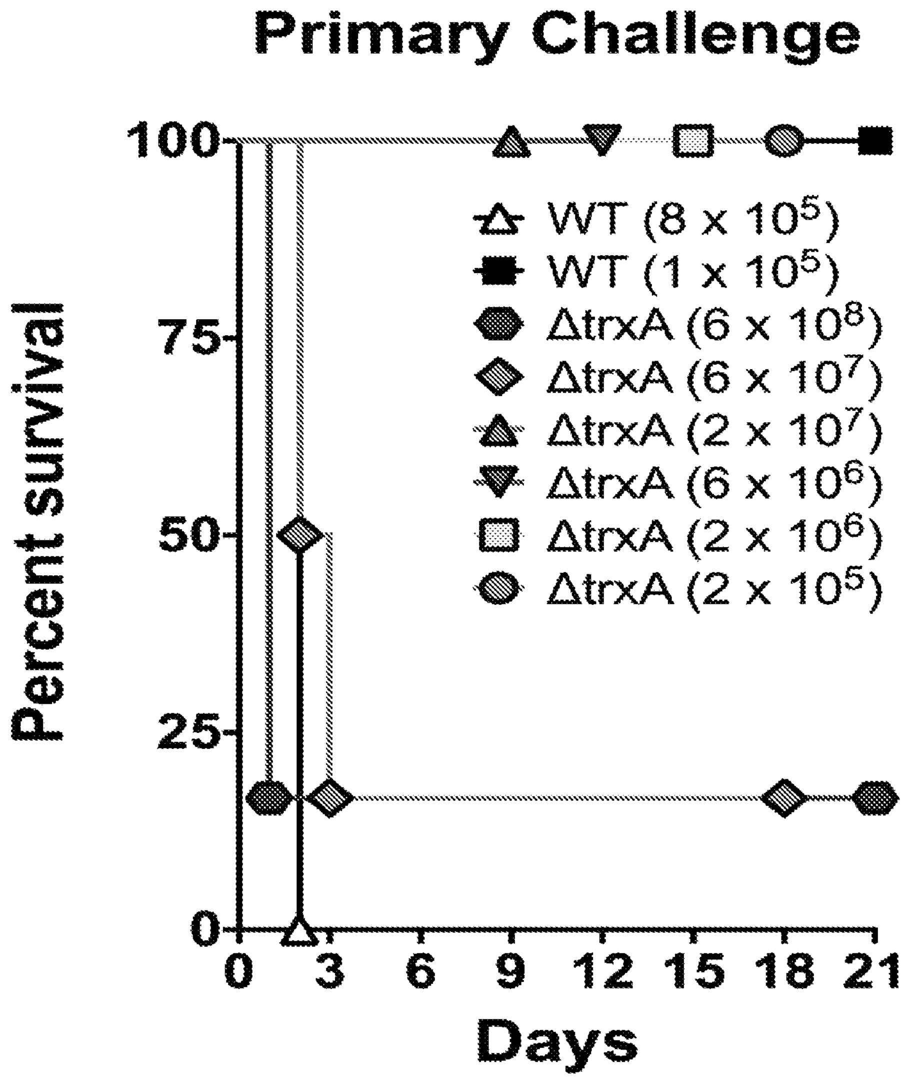
FIG. 15 shows reduced virulence of attenuated *Acinetobacter baumannii* compared to WT.

FIG. 15 shows the percent survival of mice in the primary sepsis challenge described in the FIG. 14 methodology. The virulence of attenuated *Acinetobacter baumannii* is decreased in comparison to wild type (WT) strains. Again, ΔtrxA doses of $2\times10^7$ and less showed no virulence in this assay.

Figure 16:
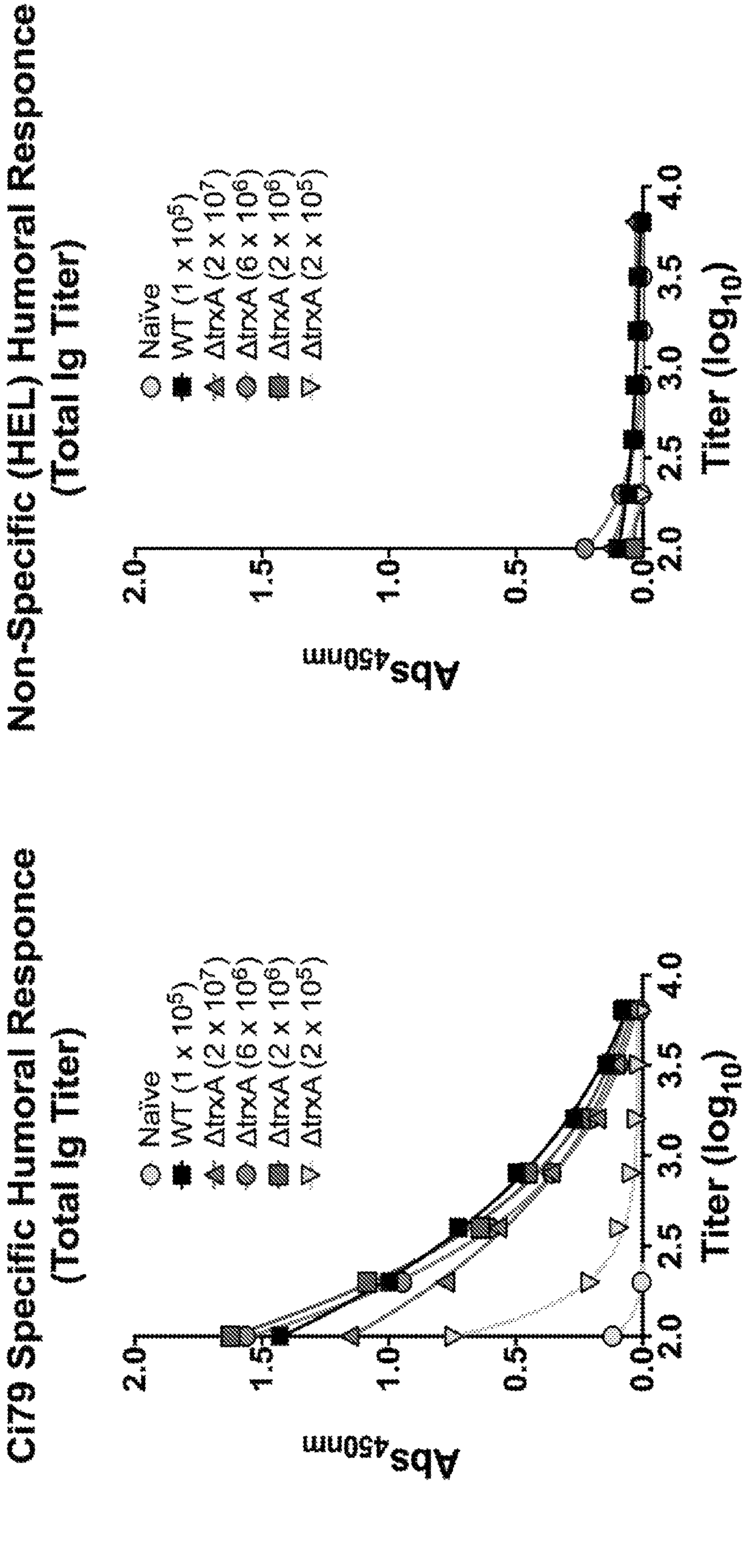
FIG. 16 shows Ci79 specific and non-specific humoral responses to a primary *Acinetobacter baumannii* sepsis.

FIG. 16 shows Ci79 specific and non-specific humoral responses to the primary challenge described in FIG. 14.

Figure 17:
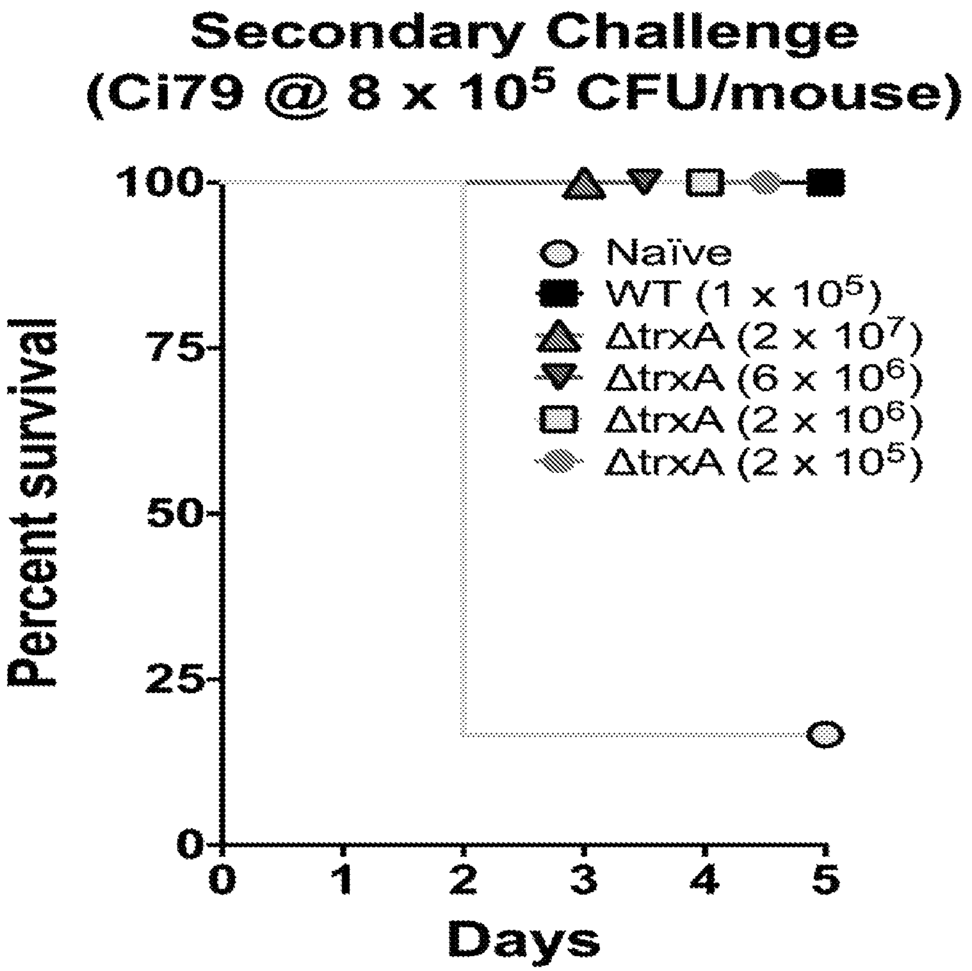
FIG. 17 shows increased survival rates by primary *Acinetobacter baumannii* sepsis challenge surviving mice in a secondary sepsis challenge.

FIG. 17 shows the percent survival of mice that survived the primary sepsis challenge in a secondary sepsis challenge as described in FIG. 14. Increased survival rates were seen in the primary sepsis challenge surviving mice compared to mice not previously exposed to any form of *Acinetobacter baumannii* (naïve).

Figure 18:
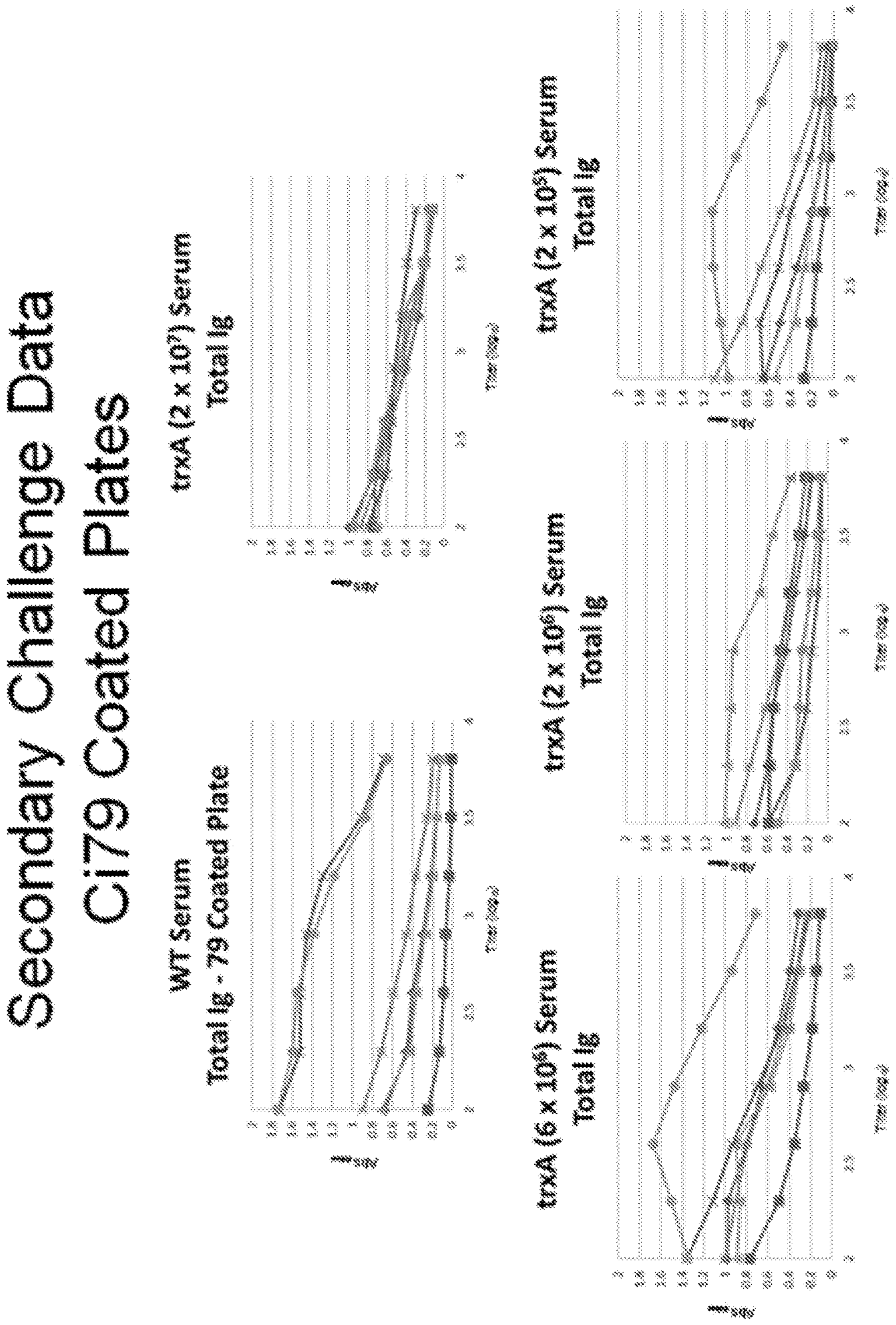
FIG. 18 shows total Ig bound to Ci79 coated plates from blood taken from mice tested in a secondary *Acinetobacter baumannii* sepsis challenge.

FIG. 18 shows total Ig bound to Ci79 coated plates from blood taken from the mice tested in the secondary challenge described in the FIG. 14 methodology.

Figure 19:
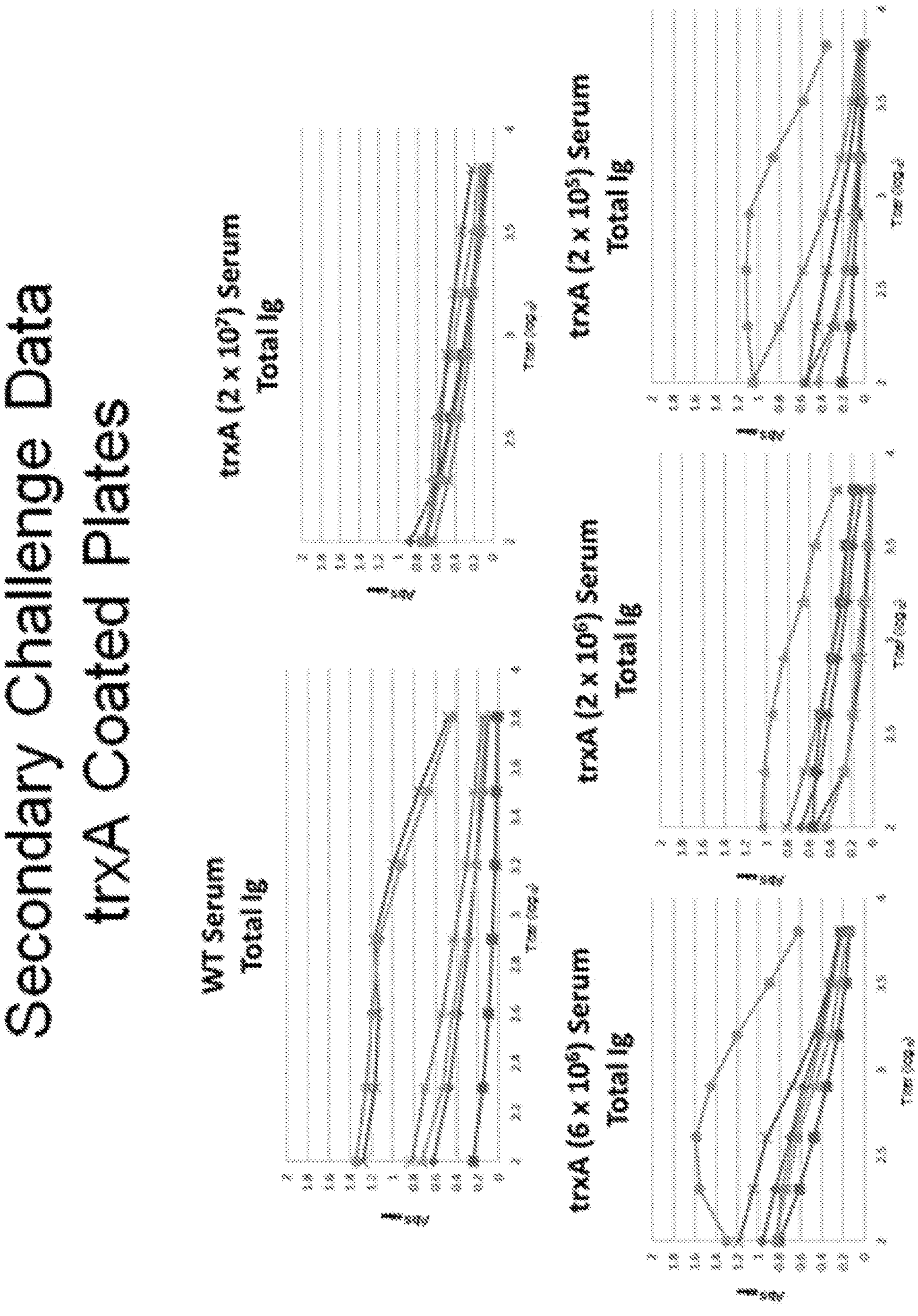
FIG. 19 shows total Ig bound to TrxA coated plates from blood taken from the mice tested in a secondary *Acinetobacter baumannii* sepsis challenge.

FIG. 19 shows total Ig bound to TrxA coated plates from blood taken from the mice tested in the secondary challenge described in the FIG. 14 methodology.

Figure 20:
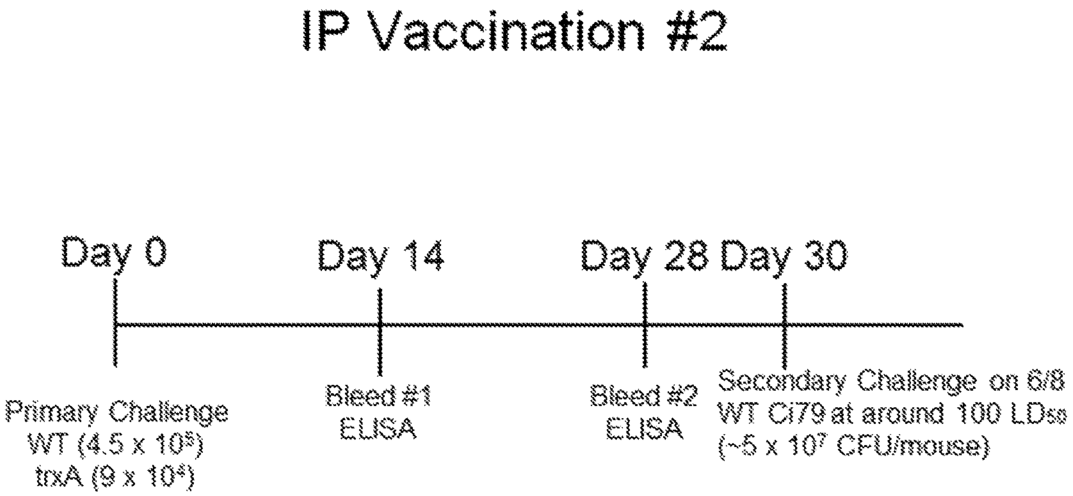
FIG. 20 shows methodology that can be used to test for Ig against Ci79 over time after initial inoculation and to test survival of mice exposed to a secondary *Acinetobacter baumannii* sepsis challenge using a 100% $LD_{50}$ amount of *Acinetobacter baumannii.*
Figures 21A, 21B:
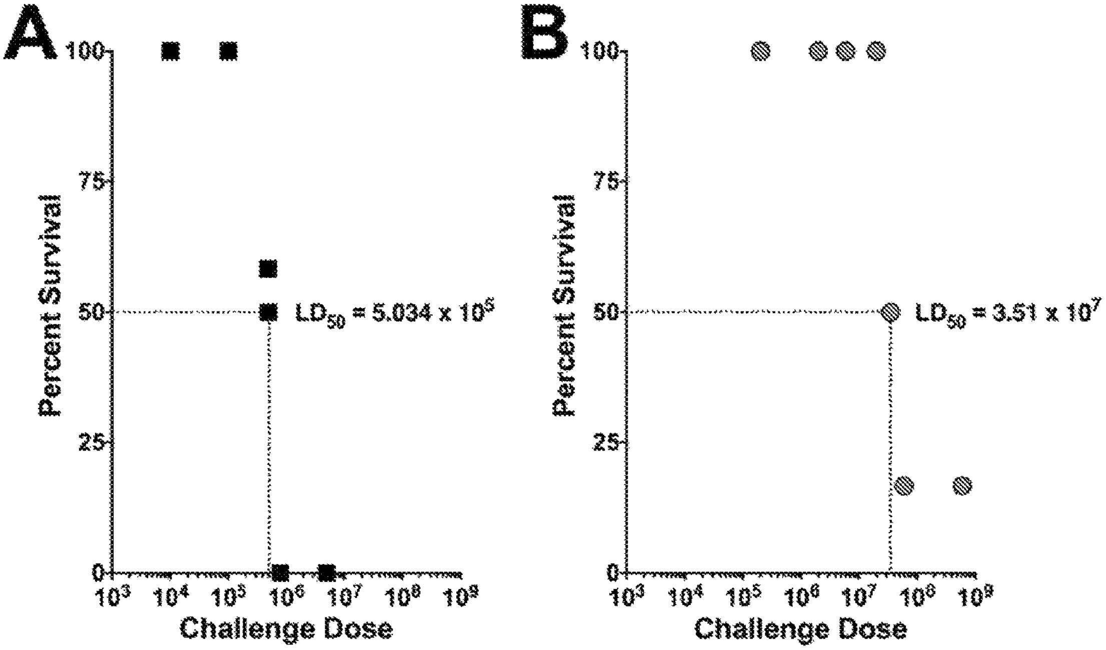
FIG. 21A-21B shows survival/virulence results upon bacterial challenge. (A) wild typ Ci79 survival. (B) ΔtrxA survival.
Figure 22:
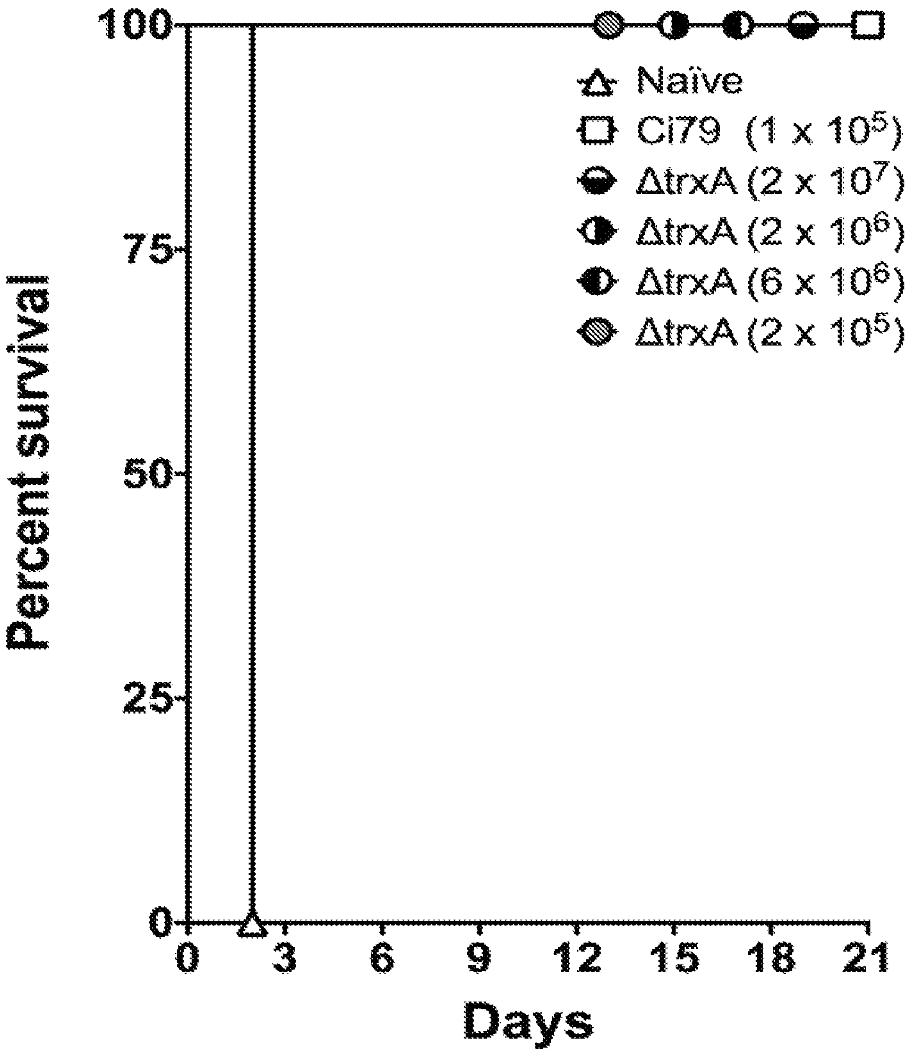
FIG. 22 shows the results of a secondary challenge with 2 LD50 of wildtype bacteria.
Figure 23:
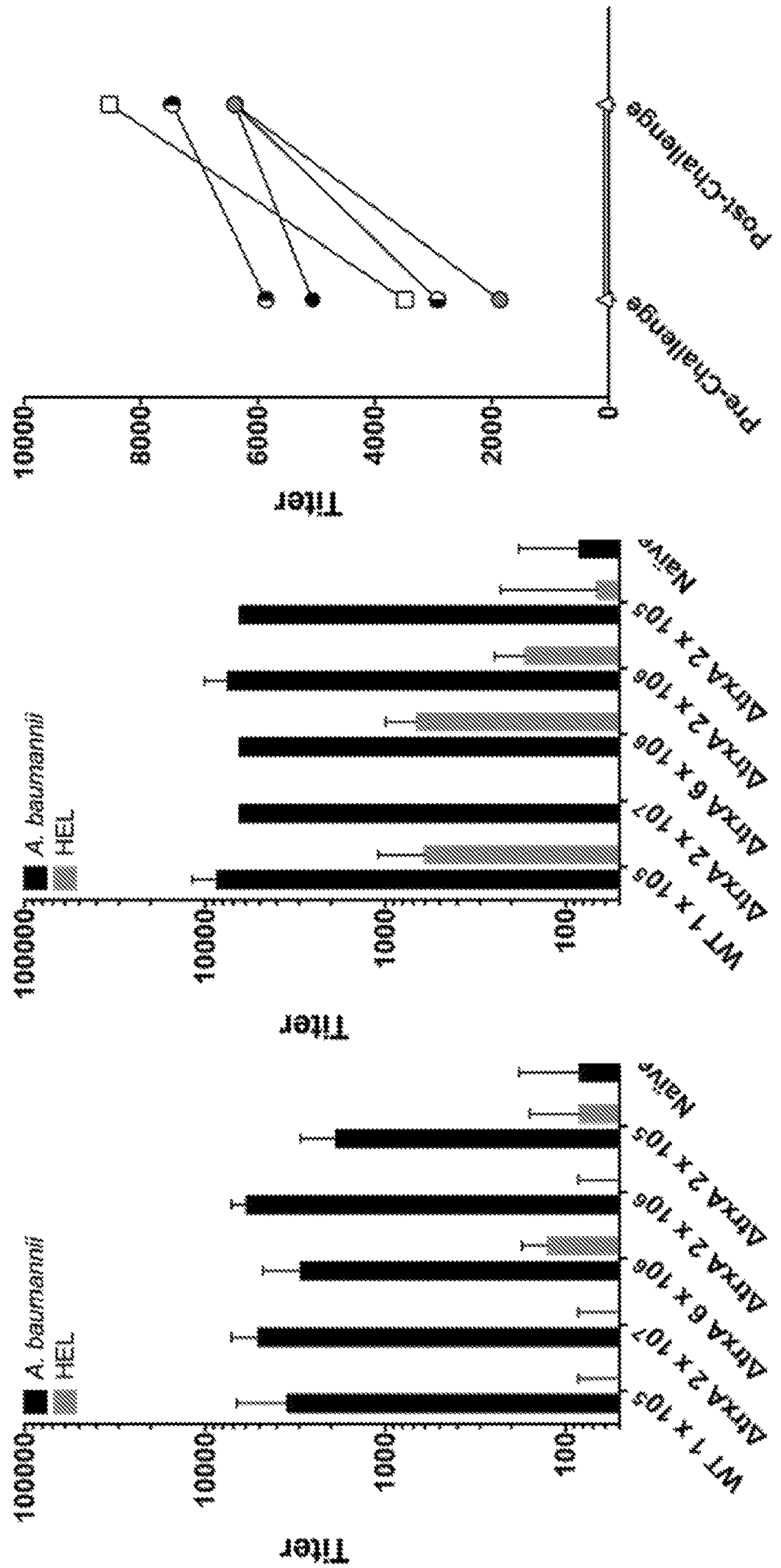
FIG. 23 shows antibody response (A) 28 days post vaccination and (B) 14 days post-secondary challenge. (C) illustration of trend line.
Figure 24:
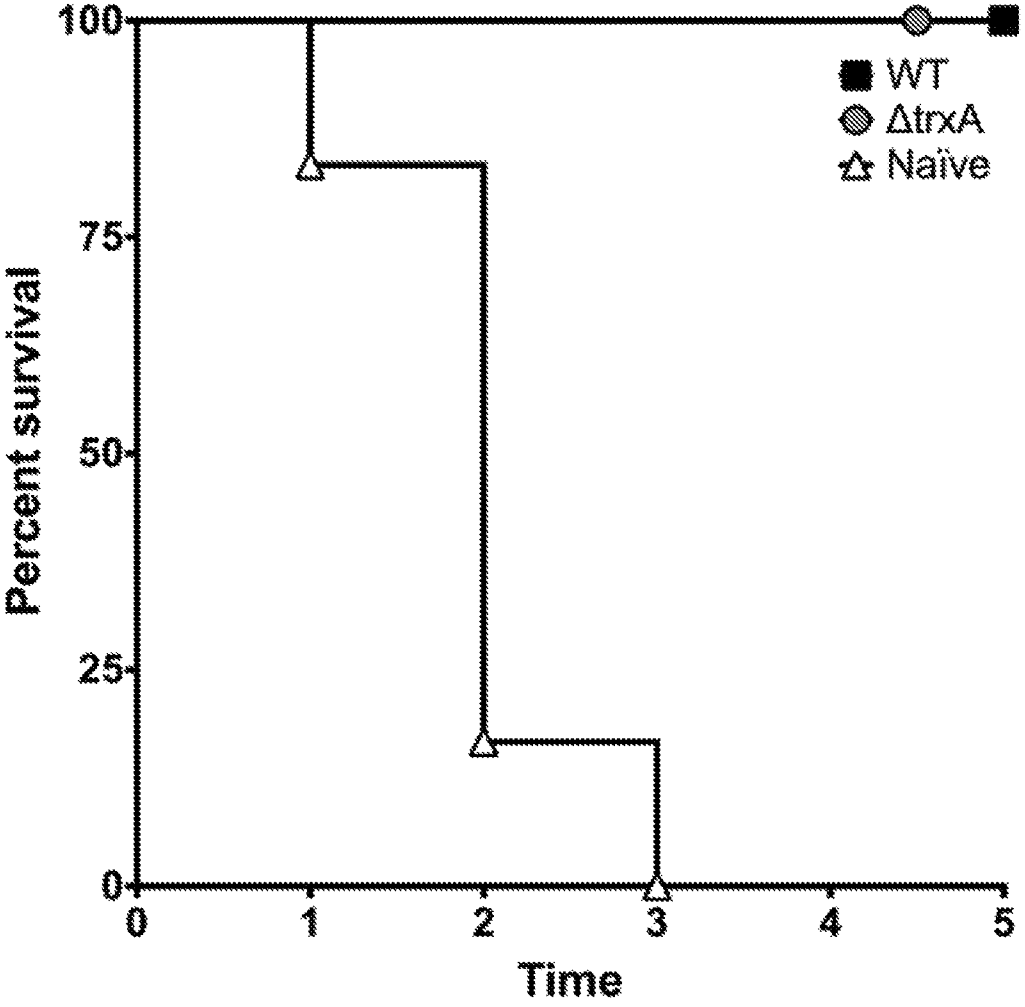
FIG. 24 shows the results of a high challenge dose of 10 LD50 of wildtype Ci79.
Figure 25:
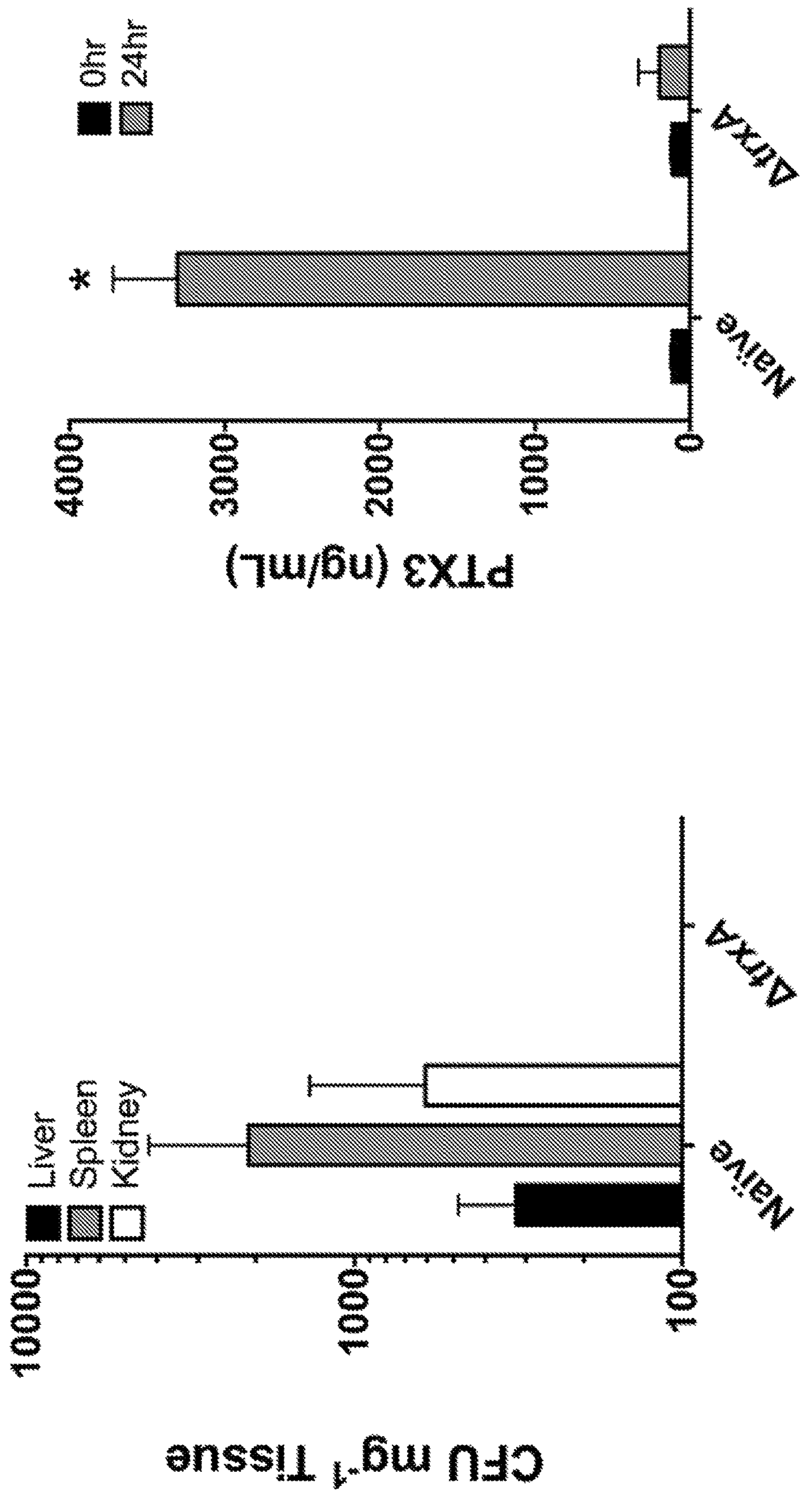
FIG. 25 shows (A) organ burden and (B) PTX3 production after high challenge dose of 10 LD50 of wildtype Ci79.
Figure 26:
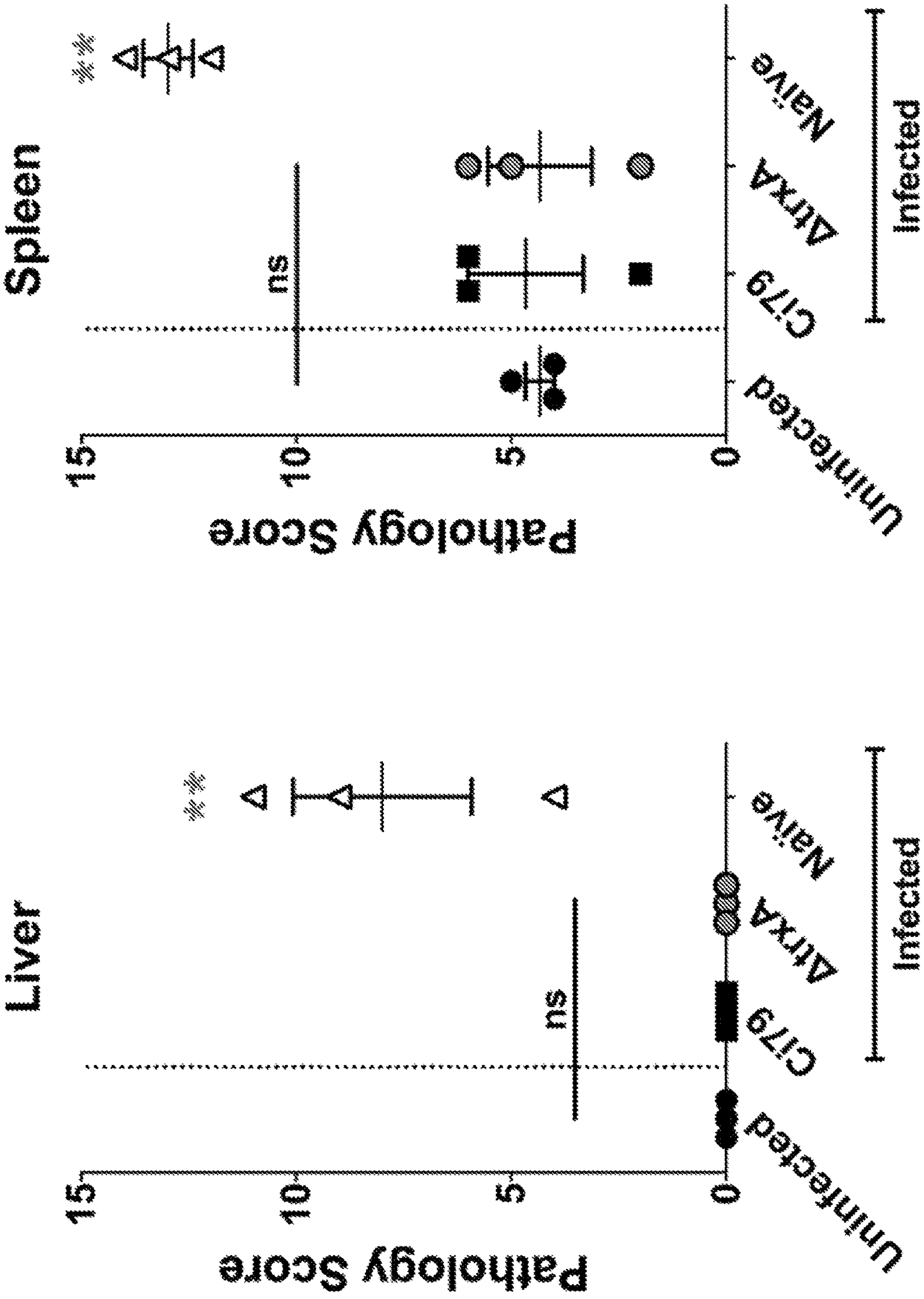
FIG. 26 shows pathology scores for (A) liver and (B) spleen from high challenge dose of 10 LD50 of wildtype Ci79.
Figure 27:
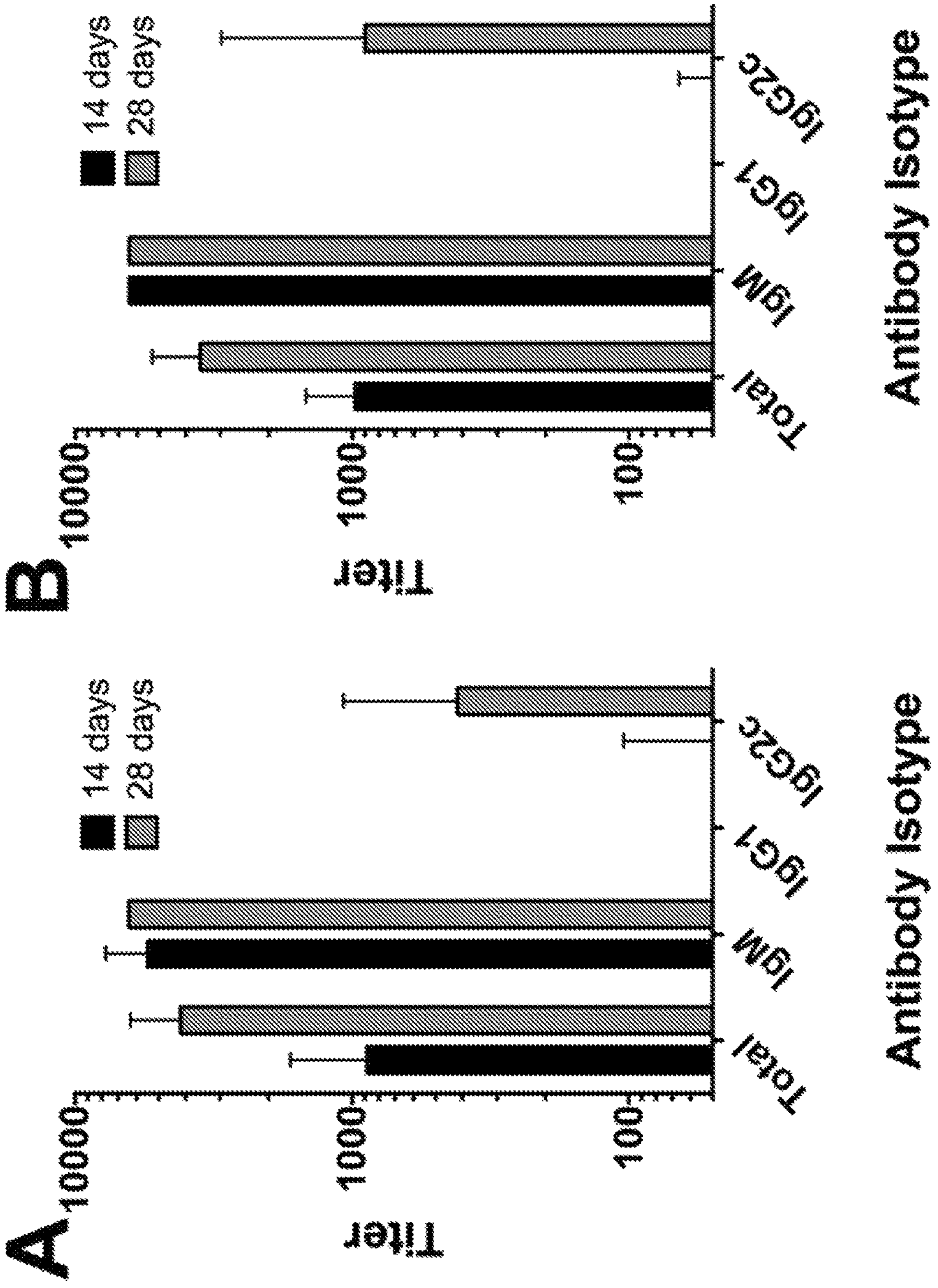
FIG. 27 shows antibody isotyping for (A) animals vaccinated with wildtype and (B) animals vaccinated with mutant at 14 and 28 days.
Figure 28:
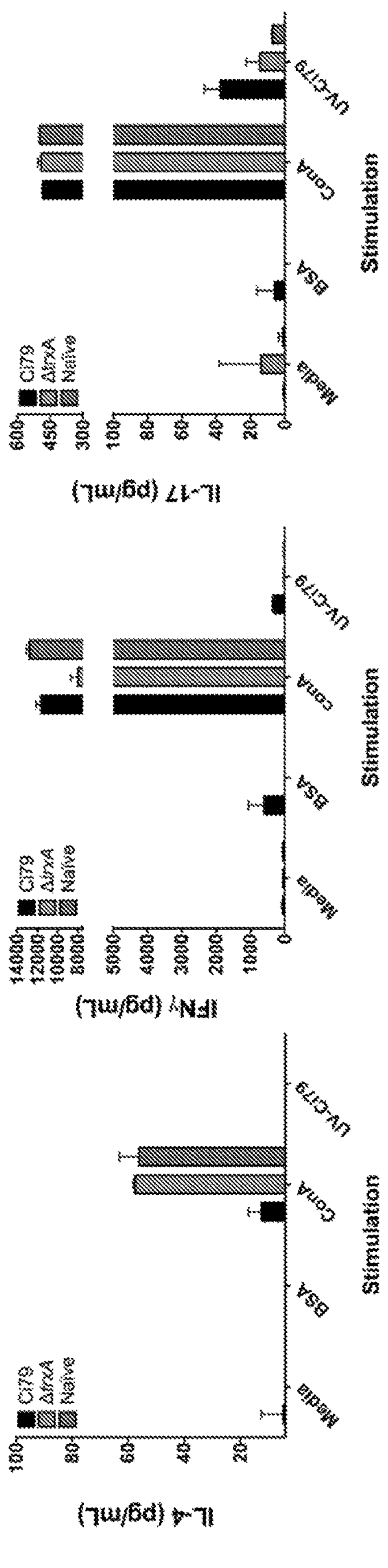
FIG. 28 shows the T cell mediated responses (A) IL-4, (B) IFNγ, and (C) IL-17.
Figure 29:
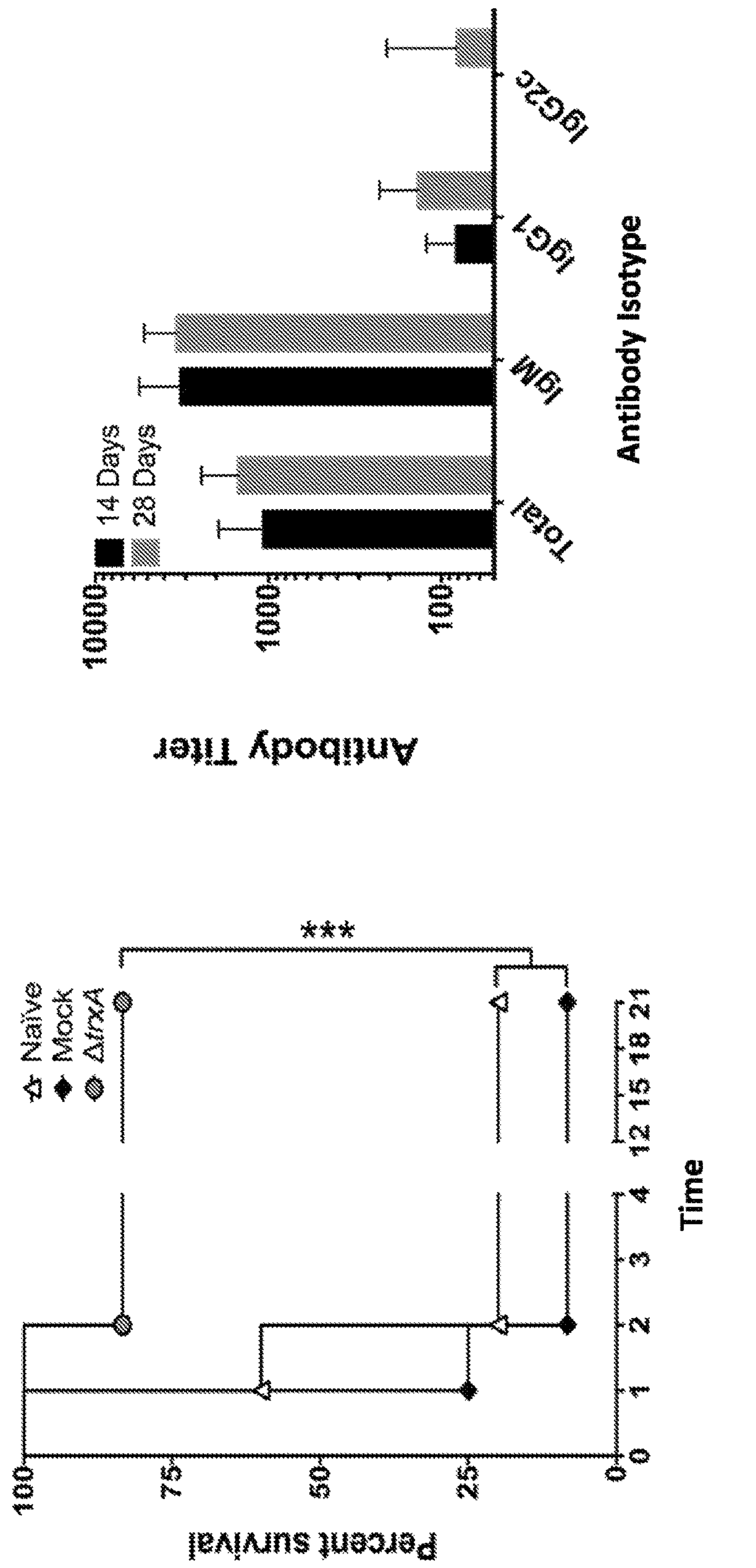
FIG. 29 shows results in the form of (A) survival and (B) antibody response for vaccination via subcutaneous administration.

FIG. 20 shows methodology for testing Ig against Ci79 over time after a primary inoculation of mice with *Acinetobacter baumannii* and attenuated *Acinetobacter baumannii* and to test survival of mice exposed to a secondary *Acinetobacter baumannii* sepsis challenge using a 100% $LD_{50}$ amount of *Acinetobacter baumannii* (approximately $5\times10^7$ CFU/mouse).

Certain embodiments are directed to a vaccine composition for prevention or treatment of bacterial infection. The compositions described herein can be administered in a number of ways depending upon whether local or systemic treatment is desired and upon the area to be treated. Administration may be topical, pulmonary (e.g., by inhalation or insufflation of powders or aerosols, including by nebulizer; intratracheal, intranasal, epidermal and transdermal), intravesical, oral, or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids, semisolids, monophasic compositions, multiphasic compositions (e.g., oil-in-water, water-in-oil), foams microsponges, liposomes, nanoemulsions, aerosol foams, polymers, fullerenes, and powders (see, e.g., Taglietti et al. (2008) *Skin Ther. Lett.* 13:6-8). Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carder compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

The compositions of the present invention may include excipients known in the art. Examples of excipients used for vaccine formulation such as adjuvents, stabilizers, preservatives, and trace products derived from vaccine manufacturing processes include but are not limited to: Aluminum Hydroxide, Amino Acids, Benzethonium Chloride, Formaldehyde or Formalin, Inorganic Salts and Sugars, Vitamins, Asparagine, Citric Acid, Lactose, Glycerin, Iron Ammonium Citrate, Magnesium Sulfate, Potassium Phosphate, Aluminum Phosphate, Ammonium Sulfate, Casamino Acid, Dimethyl-betacyclodextrin, 2-Phenoxyethanol, Bovine Extract, Polysorbate 80, Aluminum Potassium Sulfate, Gelatin, Sodium Phosphate, Thimerosal, Sucrose, Bovine Protein, Lactalbumin Hydrolysate, Formaldehyde or Formalin, Monkey Kidney Tissue, Neomycin, Polymyxin B, Yeast Protein, Aluminum Hydroxyphosphate Sulfate, Dextrose, Mineral Salts, Sodium Borate, Soy Peptone, MRC-5 Cellular Protein, Neomycin Sulfate, Phosphate Buffers, Polysorbate, Bovine Albumin or Serum, DNA, Potassium Aluminum Sulfate, Amorphous Aluminum Hydroxyphosphate Sulfate, Carbohydrates, L-histidine, Beta-Propiolactone, Calcium Chloride, Neomycin, Ovalbumin, Potassium Chloride, Potassium Phosphate, Sodium Phosphate, Sodium Taurodeoxycholate, Egg Protein, Gentamicin, Hydrocortisone, Octoxynol-10, α-Tocopheryl Hydrogen Succinate, Sodium Deoxycholate, Sodium Phosphate, Beta-Propiolactone, Polyoxyethylene 910, Nonyl Phenol (TRITON N-101, OCTOXYNOL 9), OCTOXYNOL 9 (TRITON X-100), Chick Kidney Cells, Egg Protein, Gentamicin Sulfate, Monosodium Glutamate, Sucrose Phosphate Glutamate Buffer Calf Serum Protein, Streptomycin, Mouse Serum Protein, Chick Embryo Fibroblasts, Human Albumin, Sorbitol, Sodium Phosphate Dibasic, Sodium Bicarbonate, Sorbitol, Sucrose, Potassium Phosphate Monobasic, Potassium Chloride, Potassium Phosphate Dibasic, Phenol, Phenol Red (Phenolsulfonphthalein), Amphotericin B, Chicken Protein, Chlortetracycline, Ethylenediamine-Tetraacetic Acid Sodium (EDTA), Potassium Glutamate, Cell Culture Media, Sodium Citrate, Sodium Phosphate Monobasic Monohydrate, Sodium Hydroxide, Calcium Carbonate, D-glucose, Dextran, Ferric (III) Nitrate, L-cystine, L-tyrosine, Magnesium Sulfate, Sodium Hydrogenocarbonate, Sodium Pyruvate, Xanthan, Peptone, Disodium Phosphate, Monosodium Phosphate, Polydimethylsilozone, Hexadecyltrimethylammonium Bromide Ascorbic Acid, Casein, Galactose, Magnesium Stearate, Mannitol, Hydrolyzed Porcine Gelatin, Freund's emulsified oil adjuvants (complete and incomplete), Arlacel A, Mineral oil, Emulsified peanut oil adjuvant (adjuvant 65), *Corynebacterium granulosum*-derived P40 component, Lipopolysaccharide, *Mycobacterium* and its components, Cholera toxin, Liposomes, Immunostimulating complexes (ISCOMs), Squalene, and Sodium Chloride.

Dosing may be dependent on severity and responsiveness of the condition or disease state to be treated, with the course of treatment lasting from several days to several months, or until a cure is effected or a diminution of the condition or disease state is achieved, or until optimal immune response is achieved, or until optimal protection against future infection is achieved. Optimal dosing schedules can be calculated from measurements of drug accumulation in the body of the patient. The administering professional (e.g., physician) can easily determine optimum dosages, dosing methodologies and repetition rates. Optimum dosages may vary depending on the relative potency of the agent (e.g., molecule, oligonucleotide, siRNA, antibody, virus, microbe, cell, bacterial cell), and can generally be estimated based on EC50s found to be effective in in vitro and in vivo animal models or based on the examples described herein. In general, dosage is from 0.01 μg to 100 g per kg of body weight, and may be given once or more daily, weekly, monthly or yearly. The administering professional can estimate repetition rates for dosing based on measured residence times and concentrations of the drug in bodily fluids or tissues. Following successful treatment, it may be desirable to have the subject undergo maintenance therapy to prevent the recurrence of the disease state, wherein the treatment (e.g., molecule, siRNA or antibody, virus, microbe, cell, bacterial cell) is administered in maintenance doses, ranging from 0.01 μg to 100 g per kg of body weight, once or more daily, to once every 20 years.

Embodiments of the present invention have been shown to act as a live attenuated vaccine for the prevention of infection. The present invention is not limited to a particular dose, administration route, or administration regime to a subject. The vaccine may be administered at least once; twice; three times; four times; 5-10 times; 10-20 times; 20-100 times. The method is not limited by the duration of time between each repetition of vaccine administration. The method is not limited by the duration of time between administration of the vaccine and challenge or exposure to a pathogenic agent. The duration of time may be 0 days; 1 day; 2 days; 3 days; 4 days; 5 days; 5-7 days; 1-2 weeks; 2-4 weeks; 4-8 weeks; 8-10 weeks; 10-31 weeks; 31-52 weeks; 1-5 years; 5-10 years; 10-20 years; 20-50 years; 50-100 years.

The term "pharmaceutically acceptable carrier" refers to a carrier that may be administered to a patient, together with a compound of this invention, and which does not destroy the pharmacological activity thereof and is nontoxic when administered in doses sufficient to deliver a therapeutic amount of the compound.

III. Thioredoxin and Thioredoxin Inhibitors

Thioredoxin plays a role in promoting eukaryotic cell survival, proliferation, and tumor angiogenesis, which makes it an attractive molecular target for therapeutic intervention in cancer. PX-12 (1-methylpropyl 2-imidazolyl disulfide) is a thioredoxin inhibitor that irreversibly binds rendering thioredoxin redox inactive and is being investigated as a potential cancer treatment.

The thioredoxin superfamily of proteins is characterized by a motif known as a thioredoxin fold (-C-X-X-C-) which serves as the active site of the enzyme. One of the cysteine residues forms a disulfide bond with disulfide substrate, resulting in reduction and release of one half of the molecule (which can either be an organic molecule containing a disulfide linkage or sulfur containing amino acid of an adjacent protein). The second cysteine residue of the active site then forms a disulfide bond with the first resulting in reduction of the other half of the substrate. Substrates for the above enzymes, such as asymmetric disulfide compounds, of which include but are not limited to compounds such as the imidazole disulfide PX-12, act as a substrate to these enzymes and can consequently reversibly inhibit these enzymes in a competitive fashion. In the case of thioredoxin, specifically, a third cysteine residue, $Cys^{73}$, involved in dimerization of the enzyme can also act upon imidazole disulfide compounds. Doing so, however, may result in irreversible modification of the cysteine residue and prevent dimerization of the enzyme, a process necessary to reduce the enzyme back into its active state.

In certain aspects the thioredoxin inhibitor is an asymmetric disulfide, such as but not limited to 2-(sec-Butyldisulfanyl)-1H-imidazole; 2-(sec-Butyldisulfanyl)thiazole; 2-(sec-Butyldisulfanyl)pyridine; 2-(sec-Butyldisulfanyl)-3H-imidazo[4,5-c]pyridine; 2-(sec-Butyldisulfanyl)benzo[d]thiazole; 2-(sec-Butyldisulfanyl)-6-fluorobenzo[d]thiazole; 2-(sec-Butyldisulfanyl)-6-chlorobenzo[d]thiazole; 2-(sec-Butyldisulfanyl)-6-iodobenzo[d]thiazole; 4-Bromo-2-(sec-butyldisulfanyl)benzo[d]thiazole; 5-Bromo-2-(sec-butyldisulfanyl)benzo[d]thiazole; 2-(sec-Butyldisulfanyl)-6-nitrobenzo[d]thiazole; 2-(Ethyldisulfanyl)-1H-benzo[d]imidazole; 2-(tert-Butyldisulfanyl)-1H-benzo[d]imidazole; 2-(sec-Butyldisulfanyl)-1H-benzo[d]imidazole; 2-(Isopropyldisulfanyl)-1H-benzo[d]imidazole; 2-(Cyclopentyldisulfanyl)-1H-benzo[d]imidazole; 2-(Cyclohexyldisulfanyl)-1H-benzo[d]imidazole; 2-(Cyclohexyldisulfanyl)benzo[d]thiazole; 2-(Cyclohexyldisulfanyl)benzo[d]oxazole; 2-(sec-Butyl di sulfanyl)-6-chloro-5-fluoro-1H-benzo[d]imidazole; 6-Chloro-2-(cyclohexyldisulfanyl)-5-fluoro-1H-benzo[d]imidazole; 2-(sec-Butyldisulfanyl)-5-nitro-1H-benzo[d]imidazole; 2-(Cyclohexyldisulfanyl)-5-nitro-1H-benzo[d]imidazole; 2-(Cyclohexyldisulfanyl)-5-ethoxy-1H-benzo[d]imidazole; (2-(Cyclohexyldisulfanyl)-1H-benzo[d]imidazol-6-yl)(phenyl)-methanone; 2-Amino-8-(cyclohexyldisulfanyl)-7H-purin-6-ol; 8-(Cyclohexyldisulfanyl)-7H-purin-6-amine; 2-(Cyclohexyldisulfanyl)-4H-benzo[d][1,3]thiazine; 2-(Cyclohexyldisulfanyl)-5-phenyl-1H-imidazole; or 3-(Cyclohexyldisulfanyl)-5-phenyl-4H-1,2,4-triazol-4-amine. In some aspects the thioredoxin inhibitor is 1-methylpropyl 2-imidazolyl disulfide (PX-12).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

What is claimed is:

1. An *Acinetobacter baumanni* mutant having a full or partial deletion in the thioredoxin-A (TrxA) gene that results in a non-functional TrxA gene.

2. A vaccine comprising a live attenuated *Acinetobacter baumanni*, wherein the attenuated *Acinetobacter baumanni* is *Acinetobacter baumanni* having a full or partial deletion in the thioredoxin-A (TrxA) gene that results in a non-functional TrxA gene and induces an immune response to *Acinetobacter baumanni* in a subject in need thereof.

3. The vaccine of claim 2, wherein the subject is domesticated or a livestock animal.

4. The vaccine of claim 2, wherein the vaccine is formulated for oral administration.

5. The vaccine of claim 2, wherein the vaccine is formulated for vaccination against *Acinetobacter baumanni*.

6. A method of inducing an immune response against *Acinetobacter baumanni* in a subject in need thereof comprising administering to said subject an effective dose of a live attenuated *Acinetobacter baumanni*, wherein the attenuated *Acinetobacter baumanni* is *Acinetobacter baumanni* having a full or partial deletion in the thioredoxin-A (TrxA) gene that results in a non-functional TrxA gene.

7. The method of claim 6, wherein the attenuated *Acinetobacter baumanni* is administered orally.

8. The method of claim 6, wherein the subject is domesticated or a livestock animal.

* * * * *